(12) United States Patent
Bailey

(10) Patent No.: US 9,788,789 B2
(45) Date of Patent: Oct. 17, 2017

(54) SYSTEMS, ARTICLES, AND METHODS FOR STRETCHABLE PRINTED CIRCUIT BOARDS

(71) Applicant: Thalmic Labs Inc., Kitchener (CA)

(72) Inventor: Matthew Bailey, Kitchener (CA)

(73) Assignee: THALMIC LABS INC., Kitchener (CA)

( * ) Notice: Subject to any disclaimer, the term of this patent is extended or adjusted under 35 U.S.C. 154(b) by 143 days.

(21) Appl. No.: 14/471,982

(22) Filed: Aug. 28, 2014

(65) Prior Publication Data

US 2015/0065840 A1 Mar. 5, 2015

Related U.S. Application Data

(60) Provisional application No. 61/872,569, filed on Aug. 30, 2013.

(51) Int. Cl.
*H05K 1/02* (2006.01)
*H05K 1/14* (2006.01)
(Continued)

(52) U.S. Cl.
CPC ............ *A61B 5/681* (2013.01); *A61B 5/0492* (2013.01); *A61B 5/6802* (2013.01); *H05K 1/0283* (2013.01); *A61B 5/6822* (2013.01); *A61B 5/6823* (2013.01); *A61B 5/6824* (2013.01); *A61B 5/6826* (2013.01); *A61B 5/6828* (2013.01); *A61B 5/6829* (2013.01);
(Continued)

(58) Field of Classification Search
CPC .......................... H05K 1/0281; H05K 1/0283
See application file for complete search history.

(56) References Cited

U.S. PATENT DOCUMENTS 1,411,995 A 4/1922 Dull
3,620,208 A 11/1971 Higley et al.
(Continued)

FOREIGN PATENT DOCUMENTS

DE 4412278 A1 * 10/1995 ........... H05K 1/0278
EP 0 301 790 A2 2/1989
(Continued)

OTHER PUBLICATIONS

Costanza et al., "EMG as a Subtle Input Interface for Mobile Computing," Mobile HCI 2004, LNCS 3160, edited by S. Brewster and M. Dunlop, Springer-Verlag Berlin Heidelberg, pp. 426-430, 2004.
(Continued)

*Primary Examiner* — Nathan Milakovich
(74) *Attorney, Agent, or Firm* — Seed IP Law Group LLP

(57) ABSTRACT

Improved stretchable printed circuit boards, and fabrication methods thereof, are described. The improved stretchable printed circuit boards include a serpentine conductive trace enclosed by stretchable dielectric material. The stretchable dielectric material has a serpentine shape itself, realized by crenulated edges. The crenulated edges reduce torsional strain on the conductive trace and are formed, for example, by cutting away sections of the stretchable dielectric material proximate segments of the serpentine conductive trace where the serpentine conductive trace changes direction.

2 Claims, 8 Drawing Sheets

(51) Int. Cl.
*A61B 5/00* (2006.01)
*A61B 5/0492* (2006.01)

(52) U.S. Cl.
CPC ..... *H05K 1/148* (2013.01); *H05K 2201/0154* (2013.01); *H05K 2201/09063* (2013.01); *H05K 2201/09263* (2013.01)

(56) References Cited

U.S. PATENT DOCUMENTS

| | | | |
|---|---|---|---|
| 3,880,146 A | 4/1975 | Everett et al. | |
| 4,602,639 A | 7/1986 | Hoogendoorn et al. | |
| 4,817,064 A | 3/1989 | Milles | |
| 5,003,978 A | 4/1991 | Dunseath, Jr. | |
| D322,227 S | 12/1991 | Warhol | |
| 5,081,852 A | 1/1992 | Cox | |
| 5,251,189 A | 10/1993 | Thorp | |
| D348,660 S | 7/1994 | Parsons | |
| 5,445,869 A * | 8/1995 | Ishikawa | H05K 1/028 428/209 |
| 5,482,051 A | 1/1996 | Reddy et al. | |
| 5,605,059 A | 2/1997 | Woodward | |
| 5,683,404 A | 11/1997 | Johnson | |
| 6,032,530 A | 3/2000 | Hock | |
| 6,184,847 B1 | 2/2001 | Fateh et al. | |
| 6,238,338 B1 | 5/2001 | DeLuca et al. | |
| 6,244,873 B1 | 6/2001 | Hill et al. | |
| 6,377,277 B1 | 4/2002 | Yamamoto | |
| D459,352 S | 6/2002 | Giovanniello | |
| 6,487,906 B1 | 12/2002 | Hock | |
| 6,510,333 B1 | 1/2003 | Licata et al. | |
| 6,527,711 B1 * | 3/2003 | Stivoric | A61B 5/0002 128/898 |
| 6,619,836 B1 | 9/2003 | Silvant et al. | |
| 6,720,984 B1 | 4/2004 | Jorgensen et al. | |
| 6,743,982 B2 * | 6/2004 | Biegelsen | B25J 13/084 174/69 |
| 6,807,438 B1 | 10/2004 | Brun Del Re et al. | |
| D502,661 S | 3/2005 | Rapport | |
| D502,662 S | 3/2005 | Rapport | |
| 6,865,409 B2 | 3/2005 | Getsla et al. | |
| D503,646 S | 4/2005 | Rapport | |
| 6,880,364 B1 | 4/2005 | Vidolin et al. | |
| 6,927,343 B2 * | 8/2005 | Watanabe | G01R 1/07314 174/117 F |
| 6,965,842 B2 | 11/2005 | Rekimoto | |
| 6,972,734 B1 | 12/2005 | Ohshima et al. | |
| 6,984,208 B2 | 1/2006 | Zheng | |
| 7,022,919 B2 * | 4/2006 | Brist | H05K 1/0248 174/255 |
| 7,086,218 B1 | 8/2006 | Pasach | |
| D535,401 S | 1/2007 | Travis et al. | |
| 7,173,437 B2 | 2/2007 | Hervieux et al. | |
| 7,209,114 B2 | 4/2007 | Radley-Smith | |
| D543,212 S | 5/2007 | Marks | |
| 7,265,298 B2 * | 9/2007 | Maghribi | A61N 1/0551 174/254 |
| 7,271,774 B2 | 9/2007 | Puuri | |
| 7,333,090 B2 | 2/2008 | Tanaka et al. | |
| 7,450,107 B2 | 11/2008 | Radley-Smith | |
| 7,491,892 B2 * | 2/2009 | Wagner | H05K 1/0283 174/254 |
| 7,517,725 B2 * | 4/2009 | Reis | H01L 21/67132 257/E21.599 |
| 7,558,622 B2 | 7/2009 | Tran | |
| 7,596,393 B2 | 9/2009 | Jung et al. | |
| 7,618,260 B2 | 11/2009 | Daniel et al. | |
| 7,636,549 B2 | 12/2009 | Ma et al. | |
| 7,640,007 B2 | 12/2009 | Chen et al. | |
| 7,660,126 B2 * | 2/2010 | Cho | H01R 35/02 174/254 |
| 7,809,435 B1 | 10/2010 | Ettare et al. | |
| 7,844,310 B2 | 11/2010 | Anderson | |
| 7,870,211 B2 | 1/2011 | Pascal et al. | |
| 7,925,100 B2 | 4/2011 | Howell et al. | |
| 7,948,763 B2 * | 5/2011 | Chuang | H05K 1/028 174/254 |
| D643,428 S | 8/2011 | Janky et al. | |
| D646,192 S | 10/2011 | Woode | |
| 8,054,061 B2 | 11/2011 | Prance et al. | |
| D654,622 S | 2/2012 | Hsu | |
| 8,170,656 B2 | 5/2012 | Tan et al. | |
| 8,179,604 B1 | 5/2012 | Prada Gomez et al. | |
| 8,188,937 B1 | 5/2012 | Amafuji et al. | |
| D661,613 S | 6/2012 | Demeglio | |
| 8,203,502 B1 | 6/2012 | Chi et al. | |
| 8,207,473 B2 * | 6/2012 | Axisa | B32B 37/185 174/254 |
| 8,212,859 B2 | 7/2012 | Tang et al. | |
| 8,355,671 B2 | 1/2013 | Kramer et al. | |
| 8,389,862 B2 * | 3/2013 | Arora | H01L 23/4985 174/254 |
| 8,421,634 B2 | 4/2013 | Tan et al. | |
| 8,427,977 B2 | 4/2013 | Workman et al. | |
| D682,727 S | 5/2013 | Bulgari | |
| 8,447,704 B2 | 5/2013 | Tan et al. | |
| 8,467,270 B2 | 6/2013 | Gossweiler, III et al. | |
| D689,862 S | 9/2013 | Liu | |
| 8,591,411 B2 | 11/2013 | Banet et al. | |
| D695,454 S | 12/2013 | Moore | |
| 8,620,361 B2 | 12/2013 | Bailey et al. | |
| 8,624,124 B2 * | 1/2014 | Koo | H05K 1/0219 174/117 FF |
| 8,702,629 B2 | 4/2014 | Giuffrida et al. | |
| 8,704,882 B2 | 4/2014 | Turner | |
| D716,457 S | 10/2014 | Brefka et al. | |
| D717,685 S | 11/2014 | Bailey et al. | |
| 8,879,276 B2 | 11/2014 | Wang | |
| 8,895,865 B2 * | 11/2014 | Lenahan | H05K 1/0215 174/254 |
| 8,912,094 B2 * | 12/2014 | Koo | H01L 29/78603 257/586 |
| 8,922,481 B1 | 12/2014 | Kauffmann et al. | |
| 8,925,392 B2 * | 1/2015 | Esposito | A61B 5/1036 73/862.01 |
| 8,954,135 B2 | 2/2015 | Yuen et al. | |
| 8,970,571 B1 | 3/2015 | Wong et al. | |
| 8,971,023 B2 | 3/2015 | Olsson et al. | |
| 8,973,832 B2 * | 3/2015 | Matsumura | G06K 19/07749 235/488 |
| 9,012,763 B2 * | 4/2015 | Frolov | H01L 31/0392 136/244 |
| 9,018,532 B2 * | 4/2015 | Wesselmann | H05K 1/0283 174/117 F |
| 9,086,687 B2 | 7/2015 | Park et al. | |
| D736,664 S | 8/2015 | Paradise et al. | |
| 9,146,730 B2 | 9/2015 | Lazar | |
| D741,855 S | 10/2015 | Park et al. | |
| D742,272 S | 11/2015 | Bailey et al. | |
| D742,874 S | 11/2015 | Cheng et al. | |
| D743,963 S | 11/2015 | Osterhout | |
| 9,211,417 B2 | 12/2015 | Heldman et al. | |
| D747,714 S | 1/2016 | Erbeus | |
| 9,247,637 B2 * | 1/2016 | Hsu | H05K 1/0271 |
| D750,623 S | 3/2016 | Park et al. | |
| D751,065 S | 3/2016 | Magi | |
| 9,299,248 B2 | 3/2016 | Lake et al. | |
| D756,359 S | 5/2016 | Bailey et al. | |
| 9,367,139 B2 | 6/2016 | Ataee et al. | |
| 9,372,535 B2 | 6/2016 | Bailey et al. | |
| 9,393,418 B2 | 7/2016 | Giuffrida et al. | |
| 9,439,566 B2 | 9/2016 | Arne et al. | |
| 9,450,038 B2 * | 9/2016 | Kwon | H01L 27/3276 |
| 9,472,956 B2 | 10/2016 | Michaelis et al. | |
| 9,477,313 B2 | 10/2016 | Mistry et al. | |
| 9,484,612 B2 * | 11/2016 | Sasaki | H01P 3/085 |
| 9,529,434 B2 | 12/2016 | Choi et al. | |
| 2002/0032386 A1 | 3/2002 | Sackner et al. | |
| 2002/0077534 A1 | 6/2002 | DuRousseau | |
| 2003/0036691 A1 | 2/2003 | Stanaland et al. | |
| 2003/0051505 A1 | 3/2003 | Robertson et al. | |
| 2003/0144586 A1 | 7/2003 | Tsubata | |
| 2004/0068409 A1 | 4/2004 | Tanaka et al. | |

(56) References Cited

U.S. PATENT DOCUMENTS

| | | |
|---|---|---|
| 2004/0073104 A1 | 4/2004 | Brun del Re et al. |
| 2004/0194500 A1 | 10/2004 | Rapport |
| 2004/0210165 A1 | 10/2004 | Marmaropoulos et al. |
| 2005/0005637 A1 | 1/2005 | Rapport |
| 2005/0012715 A1 | 1/2005 | Ford |
| 2005/0070227 A1 | 3/2005 | Shen et al. |
| 2005/0119701 A1 | 6/2005 | Lauter et al. |
| 2005/0177038 A1 | 8/2005 | Kolpin et al. |
| 2006/0037359 A1 | 2/2006 | Stinespring |
| 2006/0061544 A1 | 3/2006 | Min et al. |
| 2007/0132785 A1 | 6/2007 | Ebersole, Jr. et al. |
| 2008/0136775 A1 | 6/2008 | Conant |
| 2009/0007597 A1 | 1/2009 | Hanevold |
| 2009/0031757 A1 | 2/2009 | Harding |
| 2009/0040016 A1 | 2/2009 | Ikeda |
| 2009/0051544 A1 | 2/2009 | Niknejad |
| 2009/0102580 A1* | 4/2009 | Uchaykin ............. H01P 1/2039 333/185 |
| 2009/0189867 A1 | 7/2009 | Krah et al. |
| 2009/0251407 A1 | 10/2009 | Flake et al. |
| 2009/0318785 A1 | 12/2009 | Ishikawa et al. |
| 2009/0326406 A1 | 12/2009 | Tan et al. |
| 2009/0327171 A1 | 12/2009 | Tan et al. |
| 2010/0041974 A1 | 2/2010 | Ting et al. |
| 2010/0280628 A1 | 11/2010 | Sankai |
| 2010/0293115 A1 | 11/2010 | Seyed Momen |
| 2010/0317958 A1 | 12/2010 | Beck et al. |
| 2010/0330338 A1* | 12/2010 | Boyce ..................... B29C 59/02 428/156 |
| 2011/0018754 A1 | 1/2011 | Tojima et al. |
| 2011/0065319 A1* | 3/2011 | Oster ................ H01R 13/2414 439/586 |
| 2011/0134026 A1 | 6/2011 | Kang et al. |
| 2011/0166434 A1 | 7/2011 | Gargiulo |
| 2011/0172503 A1 | 7/2011 | Knepper et al. |
| 2011/0213278 A1 | 9/2011 | Horak et al. |
| 2011/0224556 A1 | 9/2011 | Moon et al. |
| 2011/0224564 A1 | 9/2011 | Moon et al. |
| 2012/0029322 A1 | 2/2012 | Wartena et al. |
| 2012/0051005 A1* | 3/2012 | Vanfleteren ........... H01L 21/565 361/749 |
| 2012/0052268 A1* | 3/2012 | Axisa ................ H01L 23/49838 428/212 |
| 2012/0101357 A1 | 4/2012 | Hoskuldsson et al. |
| 2012/0157789 A1 | 6/2012 | Kangas et al. |
| 2012/0165695 A1 | 6/2012 | Kidmose et al. |
| 2012/0188158 A1 | 7/2012 | Tan et al. |
| 2012/0203076 A1 | 8/2012 | Fatta et al. |
| 2012/0209134 A1 | 8/2012 | Morita et al. |
| 2012/0231638 A1* | 9/2012 | Ikeda .................... H01M 2/206 439/77 |
| 2012/0265090 A1 | 10/2012 | Fink et al. |
| 2012/0293548 A1 | 11/2012 | Perez et al. |
| 2012/0302858 A1 | 11/2012 | Kidmose et al. |
| 2012/0320532 A1* | 12/2012 | Wang ..................... H05K 1/189 361/720 |
| 2012/0323521 A1 | 12/2012 | De Foras et al. |
| 2013/0005303 A1 | 1/2013 | Song et al. |
| 2013/0020948 A1 | 1/2013 | Han et al. |
| 2013/0027341 A1 | 1/2013 | Mastandrea |
| 2013/0080794 A1 | 3/2013 | Hsieh |
| 2013/0127708 A1 | 5/2013 | Jung et al. |
| 2013/0165813 A1 | 6/2013 | Chang et al. |
| 2013/0191741 A1 | 7/2013 | Dickinson et al. |
| 2013/0198694 A1 | 8/2013 | Rahman et al. |
| 2013/0265229 A1 | 10/2013 | Forutanpour et al. |
| 2013/0265437 A1 | 10/2013 | Thörn et al. |
| 2013/0271292 A1 | 10/2013 | McDermott |
| 2013/0312256 A1* | 11/2013 | Wesselmann ........ H05K 1/0283 29/830 |
| 2013/0317648 A1 | 11/2013 | Assad |
| 2013/0332196 A1 | 12/2013 | Pinsker |
| 2014/0020945 A1* | 1/2014 | Hurwitz ............... H05K 1/0271 174/262 |
| 2014/0028546 A1 | 1/2014 | Jeon et al. |
| 2014/0045547 A1 | 2/2014 | Singamsetty et al. |
| 2014/0049417 A1 | 2/2014 | Abdurrahman et al. |
| 2014/0094675 A1 | 4/2014 | Luna et al. |
| 2014/0121471 A1 | 5/2014 | Walker |
| 2014/0122958 A1 | 5/2014 | Greenebrg et al. |
| 2014/0194062 A1 | 7/2014 | Palin et al. |
| 2014/0198034 A1 | 7/2014 | Bailey et al. |
| 2014/0198035 A1 | 7/2014 | Bailey et al. |
| 2014/0236031 A1 | 8/2014 | Banet et al. |
| 2014/0240103 A1 | 8/2014 | Lake et al. |
| 2014/0249397 A1 | 9/2014 | Lake et al. |
| 2014/0257141 A1 | 9/2014 | Giuffrida et al. |
| 2014/0285326 A1 | 9/2014 | Luna et al. |
| 2014/0299362 A1* | 10/2014 | Park ..................... H05K 1/0283 174/254 |
| 2014/0334083 A1 | 11/2014 | Bailey |
| 2014/0334653 A1 | 11/2014 | Luna et al. |
| 2014/0337861 A1 | 11/2014 | Chang et al. |
| 2014/0340857 A1* | 11/2014 | Hsu ..................... H05K 1/0283 361/749 |
| 2014/0349257 A1 | 11/2014 | Connor |
| 2014/0354528 A1 | 12/2014 | Laughlin et al. |
| 2014/0354529 A1 | 12/2014 | Laughlin et al. |
| 2014/0364703 A1 | 12/2014 | Kim et al. |
| 2014/0375465 A1* | 12/2014 | Fenuccio ................. G08B 5/36 340/691.1 |
| 2015/0011857 A1 | 1/2015 | Henson et al. |
| 2015/0025355 A1 | 1/2015 | Bailey et al. |
| 2015/0051470 A1 | 2/2015 | Bailey et al. |
| 2015/0057506 A1 | 2/2015 | Luna et al. |
| 2015/0057770 A1 | 2/2015 | Bailey et al. |
| 2015/0084860 A1 | 3/2015 | Aleem et al. |
| 2015/0106052 A1 | 4/2015 | Balakrishnan et al. |
| 2015/0109202 A1 | 4/2015 | Ataee et al. |
| 2015/0124566 A1 | 5/2015 | Lake et al. |
| 2015/0141784 A1 | 5/2015 | Morun et al. |
| 2015/0148641 A1 | 5/2015 | Morun et al. |
| 2015/0160621 A1 | 6/2015 | Yilmaz |
| 2015/0182113 A1 | 7/2015 | Utter, II |
| 2015/0182130 A1 | 7/2015 | Utter, II |
| 2015/0182163 A1 | 7/2015 | Utter |
| 2015/0182164 A1 | 7/2015 | Utter, II |
| 2015/0186609 A1 | 7/2015 | Utter, II |
| 2015/0216475 A1 | 8/2015 | Luna et al. |
| 2015/0230756 A1 | 8/2015 | Luna et al. |
| 2015/0234426 A1* | 8/2015 | Bailey ................... G06F 1/163 361/679.03 |
| 2015/0237716 A1* | 8/2015 | Su ....................... H05K 1/0271 174/254 |
| 2015/0261306 A1 | 9/2015 | Lake |
| 2015/0277575 A1 | 10/2015 | Ataee et al. |
| 2015/0296553 A1 | 10/2015 | DiFranco et al. |
| 2015/0325202 A1 | 11/2015 | Lake et al. |
| 2015/0370333 A1 | 12/2015 | Ataee et al. |
| 2015/0380355 A1* | 12/2015 | Rogers ................. H01L 23/538 257/773 |
| 2016/0020500 A1* | 1/2016 | Matsuda ................ H01P 3/085 333/238 |
| 2016/0150636 A1* | 5/2016 | Otsubo ................. H05K 1/028 174/254 |
| 2016/0156762 A1 | 6/2016 | Bailey et al. |
| 2016/0199699 A1 | 7/2016 | Klassen |
| 2016/0202081 A1 | 7/2016 | Debieuvre et al. |
| 2016/0309249 A1 | 10/2016 | Wu et al. |

FOREIGN PATENT DOCUMENTS

| | | |
|---|---|---|
| JP | 2009-50679 A | 3/2009 |
| KR | 20120094870 A | 8/2012 |
| KR | 20120097997 A | 9/2012 |
| WO | 2011/070554 A2 | 6/2011 |

OTHER PUBLICATIONS

Costanza et al., "Toward Subtle Intimate Interfaces for Mobile Devices Using an EMG Controller," CHI 2005, Proceedings of the

(56) References Cited

OTHER PUBLICATIONS

SIGCHI Conference on Human Factors in Computing Systems, pp. 481-489, 2005.

Ghasemzadeh et al., "A Body Sensor Network With Electromyogram and Inertial Sensors: Multimodal Interpretation of Muscular Activities," IEEE Transactions on Information Technology in Biomedicine, vol. 14, No. 2, pp. 198-206, Mar. 2010.

Gourmelon et al., "Contactless sensors for Surface Electromyography," Proceedings of the 28th IEEE EMBS Annual International Conference, New York City, NY, Aug. 30-Sep. 3, 2006, pp. 2514-2517.

International Search Report and Written Opinion, mailed May 16, 2014, for corresponding International Application No. PCT/US2014/017799, 9 pages.

International Search Report and Written Opinion, mailed Aug. 21, 2014, for corresponding International Application No. PCT/US2014/037863, 10 pages.

International Search Report and Written Opinion, mailed Nov. 21, 2014, for corresponding International Application No. PCT/US2014/052143, 9 pages.

International Search Report and Written Opinion, mailed Feb. 27, 2015, for corresponding International Application No. PCT/US2014/067443, 10 pages.

International Search Report and Written Opinion, mailed May 27, 2015, for corresponding International Application No. PCT/US2015/015675, 9 pages.

Morris et al., "Emerging Input Technologies for Always-Available Mobile Interaction," *Foundations and Trends in Human-Computer Interaction* 4(4):245-316, 2010. (74 total pages).

Naik et al., "Real-Time Hand Gesture Identification for Human Computer Interaction Based on ICA of Surface Electromyogram," IADIS International Conference Interfaces and Human Computer Interaction 2007, 8 pages.

Picard et al., "Affective Wearables," Proceedings of the IEEE $1^{st}$ International Symposium on Wearable Computers, ISWC, Cambridge, MA, USA, Oct. 13-14, 1997, pp. 90-97.

Rekimoto, "GestureWrist and GesturePad: Unobtrusive Wearable Interaction Devices," ISWC '01 Proceedings of the $5^{th}$ IEEE International Symposium on Wearable Computers, 2001, 7 pages.

Saponas et al., "Making Muscle-Computer Interfaces More Practical," CHI 2010, Atlanta, Georgia, USA, Apr. 10-15, 2010, 4 pages.

Sato et al., "Touche: Enhancing Touch Interaction on Humans, Screens, Liquids, and Everyday Objects," CHI' 12, May 5-10, 2012, Austin, Texas.

Ueno et al., "A Capacitive Sensor System for Measuring Laplacian Electromyogram through Cloth: A Pilot Study," Proceedings of the $29^{th}$ Annual International Conference of the IEEE EMBS, Cite Internationale, Lyon, France, Aug. 23-26, 2007.

Ueno et al., "Feasibility of Capacitive Sensing of Surface Electromyographic Potential through Cloth," *Sensors and Materials* 24(6):335-346, 2012.

Xiong et al., "A Novel HCI based on EMG and IMU," Proceedings of the 2011 IEEE International Conference on Robotics and Biomimetics, Phuket, Thailand, Dec. 7-11, 2011, 5 pages.

Zhang et al., "A Framework for Hand Gesture Recognition Based on Accelerometer and EMG Sensors," IEEE Transactions on Systems, Man, and Cybernetics—Part A: Systems and Humans, vol. 41, No. 6, pp. 1064-1076, Nov. 2011.

Xu et al., "Hand Gesture Recognition and Virtual Game Control Based on 3D Accelerometer and EMG Sensors," Proceedings of the 14th international conference on Intelligent user interfaces, Sanibel Island, Florida, Feb. 8-11, 2009, pp. 401-406.

Communication pursuant to Rule 164(1) EPC, dated Sep. 30, 2016, for corresponding EP Application No. 14753949.8, 7 pages.

Brownlee, "Finite State Machines (FSM): Finite state machines as a control technique in Artificial Intelligence (AI)," Jun. 2002, 12 pages.

\* cited by examiner

SYSTEMS, ARTICLES, AND METHODS FOR STRETCHABLE PRINTED CIRCUIT BOARDS

BACKGROUND

Technical Field

The present systems, articles, and methods generally relate to stretchable printed circuit boards and particularly relate to applications of stretchable printed circuit boards in wearable electronic devices.

Description of the Related Art

Stretchable Printed Circuit Boards

Typical printed circuit boards (PCBs) are substantially planar structures formed of any number of layers of dielectric material with conductive traces carried thereupon or therebetween. The dielectric material (most commonly FR4, a composite material made up of fiberglass and epoxy resin) is typically rigid, though flexible PCBs have also been developed for some applications. Flexible PCBs typically allow a degree of bendability, but neither rigid PCBs nor flexible PCBs can typically be stretched. This limitation can render rigid PCBs and flexible PCBs inadequate for applications that impose stresses/strains on the PCB itself (e.g., where a PCB is used an electrical connector between two independently movable structures).

Stretchable PCBs have been developed to enable PCB structures to adapt to physical stresses and strains. Stretchable PCBs are also typically planar structures and may have substantially the same size and geometry as rigid/flexible PCBs. However, stretchable PCBs are formed of any number of layers of stretchable dielectric material, such as rubber or silicone, with conductive traces carried thereupon or therebetween. The conductive traces are typically laid out in serpentine or crenulated paths so that, when the stretchable dielectrics are extended, the bends in the paths of the conductive traces straighten out to accommodate the extension.

FIG. 1 is a perspective view of a stretchable PCB 100 according to the state of the art. PCB 100 comprises a first dielectric layer 101 formed of stretchable dielectric material (e.g., rubber or silicone), a second dielectric layer 102 formed of stretchable dielectric material, and a serpentine conductive trace 110 carried upon the first dielectric layer 101 and sandwiched in between the first dielectric layer 101 and the second dielectric layer 102. As indicated by the horizontal arrows in the illustrated y-direction of FIG. 1, when PCB 100 is stretched in a longitudinal direction (i.e., when two opposite ends of PCB 100 are pulled apart along a length of PCB 100 in the y-direction as drawn in FIG. 1), the serpentine bends in conductive trace 110 straighten out to accommodate the stretch and electrical conduction through trace 110 is sustained despite the induced stretch.

A drawback of the design of PCB 100 is that, when PCB 100 is stretched along the y-direction in the illustrated xy-plane, conductive trace 110 experiences a torsional force in the z-direction (represented in FIG. 1 by vertical arrows in the illustrated z-direction). In other words, portions of conductive trace 110 twist or curl upwards and/or downwards in the z-direction. This twisting/curling can cause dielectric layers 101, 102 to decouple from one another and even cause trace 110 to detach from either or both of dielectric layers 101, 102. Having conductive trace 110 sandwiched in between two stretchable dielectric layers 101, 102 helps to mitigate movement of conductive trace 110 in the z-direction, but does not remove the effect entirely. What is worse, the effect is aggravated by increasing the width and/or thickness of the dielectric layers 101, 102 (and/or by increasing the stretching, of course), rendering the design of PCB 100, at best, unreliable and, at worst, inadequate for some applications. An example of an application for which this state of the art design for stretchable PCBs is inadequate is in wearable electronic devices.

Wearable Electronic Devices

Electronic devices are commonplace throughout most of the world today. Advancements in integrated circuit technology have enabled the development of electronic devices that are sufficiently small and lightweight to be carried by the user. Such "portable" electronic devices may include on-board power supplies (such as batteries or other power storage systems) and may be designed to operate without any wire-connections to other electronic systems; however, a small and lightweight electronic device may still be considered portable even if it includes a wire-connection to another electronic system. For example, a microphone may be considered a portable electronic device whether it is operated wirelessly or through a wire-connection.

The convenience afforded by the portability of electronic devices has fostered a huge industry. Smartphones, audio players, laptop computers, tablet computers, and ebook readers are all examples of portable electronic devices. However, the convenience of being able to carry a portable electronic device has also introduced the inconvenience of having one's hand(s) encumbered by the device itself. This problem is addressed by making an electronic device not only portable, but wearable.

A wearable electronic device is any portable electronic device that a user can carry without physically grasping, clutching, or otherwise holding onto the device with their hands. For example, a wearable electronic device may be attached or coupled to the user by a strap or straps, a band or bands, a clip or clips, an adhesive, a pin and clasp, an article of clothing, tension or elastic support, an interference fit, an ergonomic form, etc. Examples of wearable electronic devices include digital wristwatches, electronic armbands, electronic rings, electronic ankle-bracelets or "anklets," head-mounted electronic display units, hearing aids, and so on.

Human-Electronics Interfaces

A wearable electronic device may provide direct functionality for a user (such as audio playback, data display, computing functions, etc.) or it may provide electronics to interact with, receive information from, or control another electronic device. For example, a wearable electronic device may include sensors that detect inputs effected by a user and transmit signals to another electronic device based on those inputs. Sensor-types and input-types may each take on a variety of forms, including but not limited to: tactile sensors (e.g., buttons, switches, touchpads, or keys) providing manual control, acoustic sensors providing voice-control, electromyography sensors providing gesture control, and/or accelerometers providing gesture control.

A human-computer interface ("HCI") is an example of a human-electronics interface. The present systems, articles, and methods may be applied to HCIs, but may also be applied to any other form of human-electronics interface.

Electromyography Devices

Electromyography ("EMG") is a process for detecting and processing the electrical signals generated by muscle activity. EMG devices employ EMG sensors that are responsive to the range of electrical potentials (typically μV-mV) involved in muscle activity. EMG signals may be used in a wide variety of applications, including: medical monitoring and diagnosis, muscle rehabilitation, exercise and training, prosthetic control, as wearable electronic devices, and even in human-electronics interfaces.

BRIEF SUMMARY

A stretchable printed circuit board may be summarized as including: a first dielectric layer formed of a stretchable dielectric material; a second dielectric layer formed of a stretchable dielectric material, the second dielectric layer carried by the first dielectric layer; at least one conductive trace carried by the first dielectric layer and positioned in between the first and the second dielectric layers, wherein the at least one conductive trace forms a serpentine signal path that extends along at least a portion of a length of the stretchable printed circuit board and includes a plurality of changes in direction across a width of the stretchable printed circuit board; and a plurality of cut-away sections in the first and the second dielectric layers, wherein each cut-away section includes a respective section of the first and the second dielectric layers that is removed and each cut-away section positioned at an edge of the stretchable printed circuit board proximate and in between a respective pair of segments of the serpentine signal path where the serpentine signal path changes direction. The length of the stretchable printed circuit board may be greater than the width of the stretchable printed circuit board. The stretchable printed circuit board may further include a layer of polymer material carried by the first dielectric layer, wherein the layer of polymer material is positioned in between the first dielectric layer and the at least one conductive trace and the at least one conductive trace is carried on the layer of polymer material. The polymer material may be selected from the group consisting of: a polyamide material, a polyimide material, and a polyamide-imide material.

A stretchable printed circuit board may be summarized as including at least one conductive trace that forms a serpentine signal path, wherein the serpentine signal path extends along at least a portion of a length of the stretchable printed circuit board and includes a plurality of changes in direction across a width of the stretchable printed circuit board; and a substantially planar segment of stretchable dielectric material that encloses the at least one conductive trace, wherein the substantially planar segment of stretchable dielectric material has a crenulated shape the includes a plurality of crenulations across the at least a portion of the length of the stretchable printed circuit board, and wherein each crenulation of the substantially planar segment of stretchable dielectric material is positioned proximate and corresponds to a respective portion of the at least one conductive trace where the serpentine signal path changes direction. The substantially planar segment of stretchable dielectric material may comprise a first layer of stretchable dielectric material and a second layer of stretchable dielectric material, the second layer of stretchable dielectric material carried by the first layer of stretchable dielectric material, and the at least one conductive trace carried by the first layer of stretchable dielectric material and positioned in between the first and the second layers of stretchable dielectric material. The stretchable printed circuit board may further include a layer of polymer material, wherein the at least one conductive trace is carried on the layer of polymer material and the layer of polymer material is enclosed by the substantially planar segment of stretchable dielectric material. The polymer material may be selected from the group consisting of: a polyamide material, a polyimide material, and a polyamide-imide material.

A method of fabricating a stretchable printed circuit board may be summarized as including: depositing a first layer of stretchable dielectric material; depositing at least one conductive trace on the first layer of stretchable dielectric material, wherein the at least one conductive trace forms a serpentine signal path that extends along at least a portion of a length of the stretchable printed circuit board and includes a plurality of changes in direction across a width of the stretchable printed circuit board; depositing a second layer of stretchable dielectric material on the at least one conductive trace; and cutting away sections in the first and the second layers of stretchable dielectric material, each cut-away section positioned at an edge of the stretchable printed circuit board proximate at least one respective change in direction in the serpentine signal path. Depositing at least one conductive trace on the first layer of stretchable dielectric material may include: forming a flexible printed circuit board, wherein forming a flexible printed circuit board comprises: depositing a layer of polymer material; depositing a layer of conductive metal on the layer of polymer material; patterning the layer of conductive metal to provide at least one conductive trace having a serpentine signal path; and patterning the layer of polymer material; and depositing the flexible printed circuit board on the first layer of stretchable dielectric material. The polymer material may be selected from the group consisting of: a polyamide material, a polyimide material, and a polyamide-imide material.

A method of fabricating a stretchable printed circuit board may be summarized as including: fabricating a flexible printed circuit board, wherein fabricating a flexible printed circuit board comprises: depositing a layer of flexible dielectric material; depositing a layer of conductive metal on top of the flexible dielectric material; and etching a circuit pattern into the layer of conductive metal, wherein the circuit pattern includes at least one serpentine conductive trace that includes a plurality of changes in direction, removing at least some portions of the flexible dielectric material that are not covered by the at least one serpentine conductive trace; and enclosing at least a portion of the flexible printed circuit board in a stretchable dielectric material, wherein the stretchable dielectric material forms a crenulated shape that includes a plurality of crenulations across a length thereof, wherein each crenulation is positioned proximate and corresponds to a respective change in direction in the at least one serpentine conductive trace. Enclosing the flexible printed circuit board in a stretchable dielectric material may include: placing the flexible printed circuit board into a mold that provides a crenulated shape for the stretchable dielectric material; injecting the stretchable dielectric material, in liquid form, into the mold; solidifying the stretchable dielectric material; and removing the mold. Enclosing the flexible printed circuit board in a stretchable dielectric material may include: depositing a first layer of stretchable dielectric material; depositing the flexible printed circuit board on the first layer of stretchable dielectric material; depositing a second layer of stretchable dielectric material on the first layer of stretchable dielectric material, wherein the flexible printed circuit board is positioned in between the first and the second layers of stretchable dielectric material; and cutting away sections in the first and the second layers of stretchable dielectric material, each cut-away section positioned at an edge of the stretchable printed circuit board proximate at least one respective change in direction in the at least one serpentine conductive trace of the flexible printed circuit board.

A wearable electronic device may be summarized as including: a first pod structure, wherein the first pod structure includes a first sensor to in use detect an input from a user and a first electric circuit; a second pod structure, wherein the second pod structure includes a second electric circuit, and wherein the first and the second pod structures are physically spaced apart from one another; and at least one stretchable printed circuit board that electrically couples the first electric circuit of the first pod structure with the second electric circuit of the second pod structure, wherein the at least one stretchable printed circuit board comprises: at least one conductive trace that forms a serpentine signal path, wherein the serpentine signal path extends along at least a portion of a length of the stretchable printed circuit board and includes a plurality of changes in direction across a width of the stretchable printed circuit board; and a substantially planar segment of stretchable dielectric material that encloses the at least one conductive trace, wherein the substantially planar segment of stretchable dielectric material has a crenulated shape that includes a plurality of crenulations across the length of the stretchable printed circuit board, and wherein each crenulation of the substantially planar segment of stretchable dielectric material is positioned proximate and corresponds to a respective portion of the at least one conductive trace where the serpentine signal path changes direction.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn are not intended to convey any information regarding the actual shape of the particular elements, and have been solely selected for ease of recognition in the drawings.

DETAILED DESCRIPTION

Figure 1:
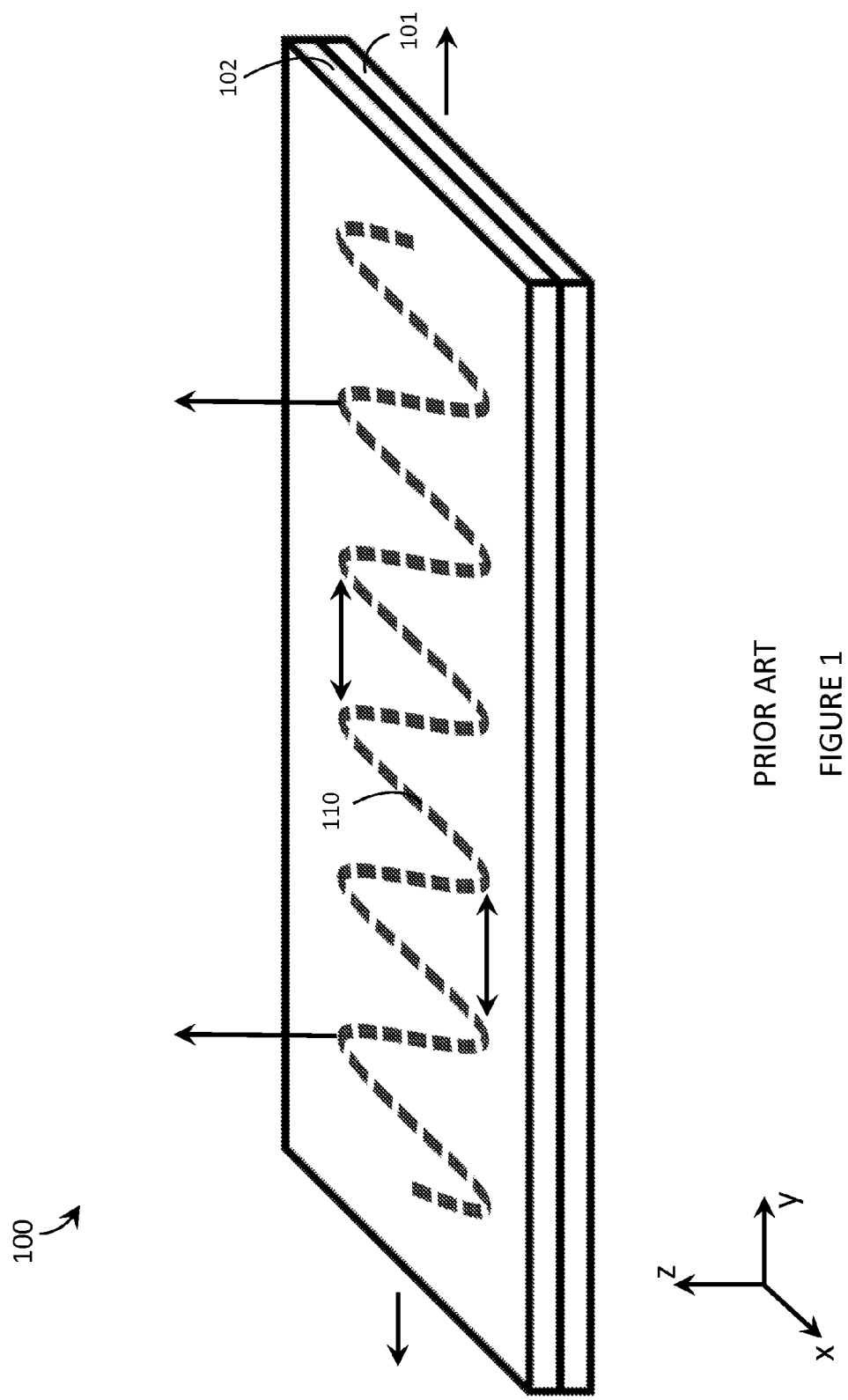
FIG. 1 is a perspective view of a stretchable PCB according to the state of the art.

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with electronic devices, and in particular portable electronic devices such as wearable electronic devices, have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment" or "an embodiment" means that a particular feature, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its broadest sense, that is as meaning "and/or" unless the content clearly dictates otherwise.

The headings and Abstract of the Disclosure provided herein are for convenience only and do not interpret the scope or meaning of the embodiments.

The various embodiments described herein provide systems, articles, and methods for improved stretchable PCBs. Specifically, the present systems, articles, and methods provide stretchable PCB designs (and fabrication methods thereof) that reduce the torsional force in the z-direction experienced by a conductive trace when a PCB is stretched in the xy-plane.

Throughout this specification and the appended claims, the term "stretchable" (as in, "stretchable PCB" or "stretchable dielectric material") is generally used to refer to a structure or material that permits a substantial increase in its length, width, and/or height in at least one spatial direction without loss of structural integrity. A substantial increase is understood to include an increase by at least 10% and may include an increase of 50%, 100%, or more. In accordance with the present system, articles, and methods, a stretchable PCB may be elastic (meaning it may naturally return to its unstretched state once the stretching force is removed) and/or flexible.

A flexible PCB is characterized by its ability to be bent or curved in an out-of-plane direction, so that if the flexible PCB lies in the xy-plane then it may be bent or curved in the z-direction. Flexible PCBs are not inherently stretchable, but in accordance with the present systems, articles, and methods a stretchable PCB may be flexible and may, for example, incorporate an adapted flexible PCB in its structure. The adapted flexible PCB may include one or more serpentine conductive trace(s) carried on a layer of polymer material, the serpentine nature of the conductive trace(s) characterized by a plurality of changes in direction. Throughout this specification and the appended claims, the term "serpentine" is used to denote a path or geometry that has a length greater than its width, and for which the length generally follows a circuitous pattern relative to the width that, in various implementations, may be described as meandering, a zig-zag, boustrophedonic, back-and-forth, and/or tortuous. Portions of the layer of polymer material may be patterned to produce serpentine segments that underlie the serpentine conductive traces. The adapted flexible PCB may then be incorporated into a stretchable PCB by enclosing the flexible PCB in a stretchable dielectric material, such as rubber or silicone. As described in more detail later, the torsional forces on the serpentine conductive trace(s) when the stretchable PCB is stretched may be reduced by cutting away sections of the stretchable dielectric material (or otherwise molding/patterning/shaping the stretchable dielectric material to include crenulations) that are proximate segments of the serpentine conductive traces where the serpentine conductive traces change direction, so that the stretchable dielectric material follows the serpentine paths of the conductive traces.

Figure 2:
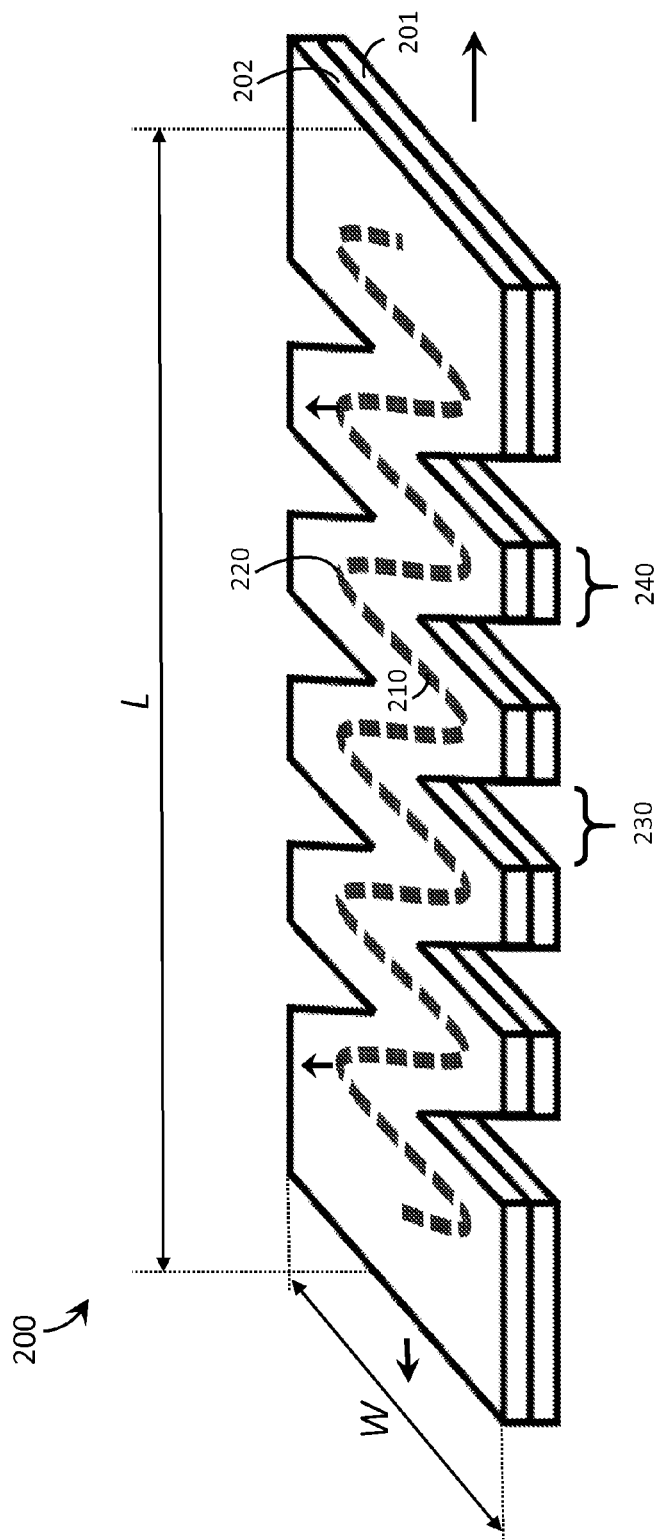
FIG. 2 is a perspective view of an improved stretchable PCB in accordance with the present systems, articles, and methods.

FIG. 2 is a perspective view of an improved stretchable PCB 200 in accordance with the present systems, articles, and methods. PCB 200 comprises a first dielectric layer 201 formed of stretchable dielectric material (e.g., rubber or silicone), a second dielectric layer 202 formed of stretchable dielectric material, and a serpentine conductive trace 210 carried upon the first dielectric layer 201 and positioned (i.e., sandwiched) in between the first dielectric layer 201 and the second dielectric layer 202. Serpentine conductive trace 210 extends along at least a portion of a length (labeled L in FIG. 2) of stretchable PCB 200 in the y-direction and includes a plurality of changes in direction 220 (only one called out in FIG. 2 to reduce clutter) across a width (labeled W in FIG. 2) of stretchable PCB 200 in the x-direction.

The first and the second dielectric layers 201, 202 include a plurality of cut-away sections 230 (only one called out in FIG. 2 to reduce clutter) corresponding to respective sections of the first and the second dielectric layers 201, 202 that are removed (by, for example, a die-cut process). That is, each cut-away section includes a respective portion of both the first dielectric layer 201 and the second dielectric layer 202. Each cut-away section 230 is positioned at an edge of stretchable PCB 200 proximate and in between a respective pair of segments of serpentine conductive trace 210 where serpentine conductive trace 210 changes direction (i.e., in between segments that each correspond to a respective change in direction 220). In this way, the material width of PCB 200 is reduced (relative to, for example, PCB 100 from FIG. 1) in the vicinity of the changes in direction 220 of trace 210. The torsional (i.e., "twisting" or "curling") force imposed on conductive trace 210 when PCB 200 is stretched is dependent on the width of the stretchable dielectric material 201, 202, and therefore the use of cut-away sections 230 reduces the torsional force on conductive trace 210 when PCB 200 is stretched. Thus, PCB 200 provides a more reliable and more stretchable PCB compared to the state of the art (i.e., compared to PCB 100 from FIG. 1).

The reduction in the torsional forces on conductive trace 210 of PCB 200 compared to the torsional forces on conductive trace 110 of PCB 100 (due, at least in part, to the inclusion of cut-away sections 230 in PCB 200) is represented by smaller vertical arrows in the z-direction in FIG. 2 compared to the analogous vertical arrows in the z-direction in FIG. 1.

As shown in FIG. 2, the length of stretchable PCB 200 may be greater than the width of stretchable PCB 200.

In accordance with the present systems, articles, and methods, PCB 200 may be fabricated by first fabricating a state-of-the-art stretchable PCB such as PCB 100 from FIG. 1 and then removing (e.g., by cutting away, extracting, etching off, die-cutting, etc.) cut-away sections 230 at one or more edge(s) of PCB 200 proximate and in between respective pairs of segments of serpentine conductive trace 210 where serpentine conductive trace 210 changes direction (i.e., segments 220). The cut-away sections 230 of PCB 200 produce a plurality of crenulations 240 (only one called out in FIG. 2 to reduce clutter) in PCB 200 that give PCB 200 itself a serpentine or crenulated shape. Throughout this specification and the appended claims, the term "crenulation" and variants such as "crenulated" are used to describe a particular formation of one or more outer edge(s) of a geometry or structure. A "crenulation" or "crenulated shape" has one or more edge(s) patterned to provide an at least approximately repeated variation between relatively narrower and wider portions across a length of the geometry or structure. In accordance with the present systems, articles, and methods, "crenulations" and/or a "crenulated shape" may include one or more edge(s) that is/are scalloped, serrated, notched, saw-toothed, and/or indented.

Stretchable PCB 200 comprises a serpentine conductive trace 210 that extends along at least a portion of a length thereof, (where serpentine conductive trace 210 includes a plurality of changes in direction across a width of PCB 200), and a substantially planar segment of stretchable dielectric material 201, 202 that encloses serpentine conductive trace 210. The substantially planar segment of stretchable dielectric material 201, 202 has a crenulated shape that also includes a plurality of crenulations 240 across the length of PCB 200, with each crenulation 240 positioned proximate and corresponding to (i.e., including) a respective portion or segment 220 of serpentine conductive trace 210 where serpentine conductive trace 210 changes direction.

In accordance with the present systems, articles, and methods, the exact shape/geometry of a serpentine conductive trace (e.g., 210), a cut-away section (i.e., 230), and or a crenulation (e.g., 240) may vary in different applications. For example, PCB 200 is illustrated with serpentine conductive trace 210 having rounded curves at segments 220 where serpentine conductive trace 210 changes direction, cut-away sections 230 having triangular or "V" shapes, and crenulations 240 being tapered towards the outer edges of PCB 200, but any or all of these geometries/configurations may vary in alternative implementations.

Figure 3:
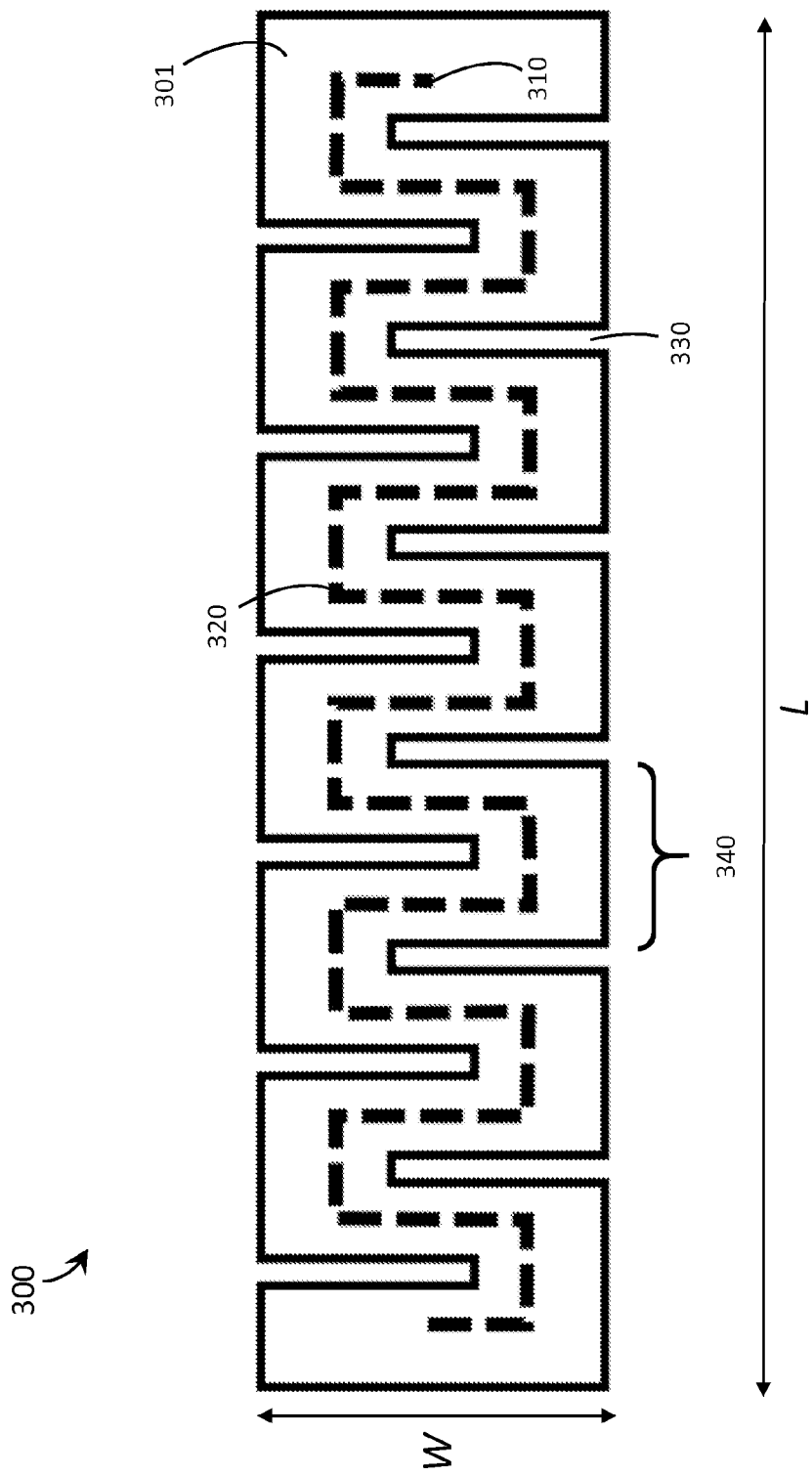
FIG. 3 is a top plan view of an improved stretchable PCB in accordance with the present systems, articles, and methods showing exemplary alternative shapes/geometries for various features compared to the PCB from FIG. 2.

FIG. 3 is a top plan view of an improved stretchable PCB 300 in accordance with the present systems, articles, and methods showing exemplary alternative shapes/geometries for various features compared to PCB 200 from FIG. 2. PCB 300 includes a stretchable dielectric material 301 that encloses a serpentine conductive trace 310. Serpentine conductive trace 310 extends along a length (labeled as L in FIG. 3) of PCB 300 and includes a plurality of changes in direction 320 across a width (labeled as W in FIG. 3) of PCB 300. In PCB 300, the changes in direction 320 are realized by right-angle turns (e.g., with the appearance of crenulations) as opposed to the rounded curves 220 of PCB 200 from FIG. 2. Stretchable dielectric material 301 has a crenulated shape that includes similarly right-angled crenulations 340 produced by straight, rectangular cut-away sections 330.

As previously described, serpentine conductive trace 310 may comprise an adapted flexible PCB including a polymer material (or similar material, not visible in FIG. 3) layer that carries a conductive metal layer. In order to adapt a flexible PCB for use in a stretchable PCB in accordance with the present systems, articles, and methods, the layer of polymer material may be patterned to remove most or all of the polymer material that is not covered by conductive metal and the conductive metal may provide serpentine conductive traces. Thus, the layer of polymer material may include serpentine formations as well.

Throughout this specification and the appended claims, reference is often made to a "polymer material," such as the "layer of polymer material" described above. The term "polymer material" is used to generally capture any material having the electrically insulative, physically flexible, and/or physically stretchable properties required in the present systems, articles, and methods. Specific examples of polymer materials that are well-suited for use in the present systems, articles, and methods include polyamide materials, polyimide materials, and polyamide-imide materials.

In FIGS. 1, 2, and 3, conductive traces 110, 210, and 310 are shown in dashed lines to represent the fact that conductive traces 110, 210, and 310 are enclosed by stretchable dielectric material and may not actually be visible in the illustrated views. For example, conductive traces 110, 210, and 310 may only be visible if the corresponding stretchable dielectric material by which they are enclosed is at least partially optically transparent. Any or all of conductive traces 110, 210, and/or 310 may be enclosed by stretchable dielectric material that is optically transparent, optically semi-transparent, or optically opaque (i.e., any or all of stretchable dielectric materials 101, 102, 201, 202, and/or 301 may be optically transparent, optically semi-transparent, or optically opaque).

The stretchable PCBs described herein (e.g., PCB 200 and/or PCB 300) may include and/or electrically couple to discrete electrical/electronic components. In some implementations, the stretchable PCBs described herein may include one or more electrical connector(s) positioned at discrete positioned along a length thereof (e.g., a first electrical connector at a first end of the PCB and a second connector at a second end of the PCB) and the stretchable PCB may provide stretchable electrically conductive coupling to/from the one or more electrical connector(s).

In addition to improved stretchable PCBs themselves, the present systems, articles, and methods describe methods of fabricating, manufacturing, and/or producing improved stretchable PCBs.

Figure 4:
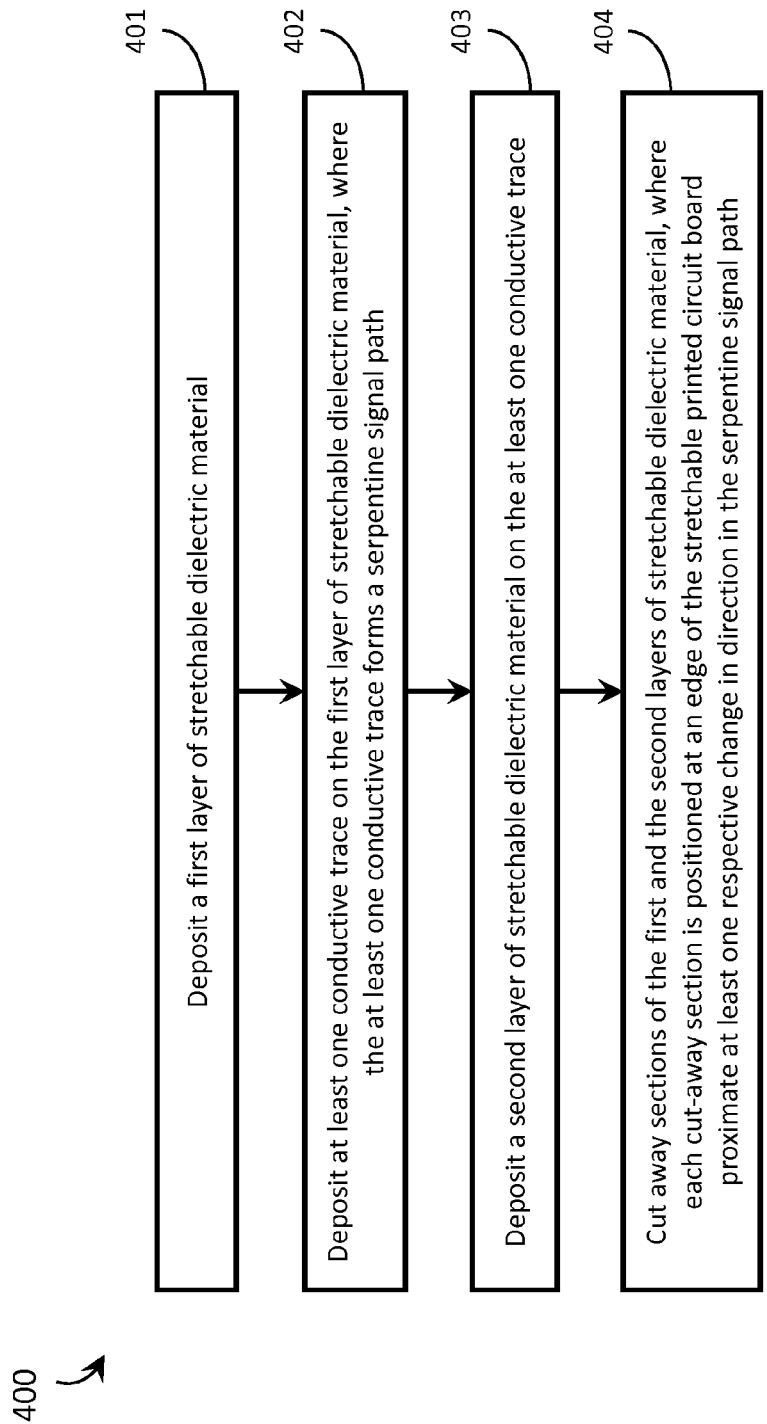
FIG. 4 is a flow-diagram showing a method of fabricating a stretchable PCB in accordance with the present systems, articles, and methods.

FIG. 4 is a flow-diagram showing a method 400 of fabricating a stretchable PCB in accordance with the present systems, articles, and methods. Method 400 includes four acts 401, 402, 403, and 404, though those of skill in the art will appreciate that in alternative embodiments certain acts may be omitted and/or additional acts may be added. Those of skill in the art will also appreciate that the illustrated order of the acts is shown for exemplary purposes only and may change in alternative embodiments. Method 400 may be performed using conventional tools and equipment for fabricating, manufacturing, or otherwise producing PCBs.

At 401, a first layer of stretchable dielectric material is deposited. The first layer of stretchable dielectric material may include, for example, rubber and/or silicone.

At 402, at least one conductive trace is deposited on the first layer of stretchable dielectric material. The at least one conductive trace forms a serpentine signal path along a length of the first layer of dielectric material, where the serpentine signal path includes a plurality of changes in directions across a width of the first layer of stretchable dielectric material.

At 403, a second layer of stretchable dielectric material is deposited on the at least one conductive trace. The second layer of stretchable dielectric material may include, for example, rubber and/or silicone. Together, the first and the second layers of stretchable dielectric material enclose, encapsulate, encompass, laminate, or otherwise surround at least a portion of the at least one conductive trace.

At 404, sections of the first and the second layers of stretchable dielectric material are cut away, where each cut-away section is positioned at an edge of the stretchable printed circuit board proximate at least one respective change in direction in the serpentine signal path of the at least one conductive trace.

As previously described, depositing at least one conductive trace at 402 may include depositing a layer of conductive metal on the first layer of stretchable dielectric material and patterning the layer of conductive metal using, for example, a lithography process to form the serpentine signal path of the at least one conductive trace. Alternatively, depositing at least one conductive trace at 402 may include forming an adapted flexible PCB that includes at least one serpentine conductive trace and from which excess (i.e., uncovered by conductive metal) polymer material (or similar) is removed such that the remaining polymer material (or similar) also includes serpentine segments underlying serpentine segments of the conductive trace. In such cases, depositing at least one conductive trace at 402 may include: forming a flexible PCB, wherein forming a flexible PCB comprises: depositing a layer of polymer material; depositing a layer of conductive metal on the layer of polymer material; patterning the layer of conductive metal to provide at least one conductive trace having a serpentine signal path; and patterning the layer of polymer material; and depositing the flexible PCB on the first layer of stretchable dielectric material.

Figure 5:
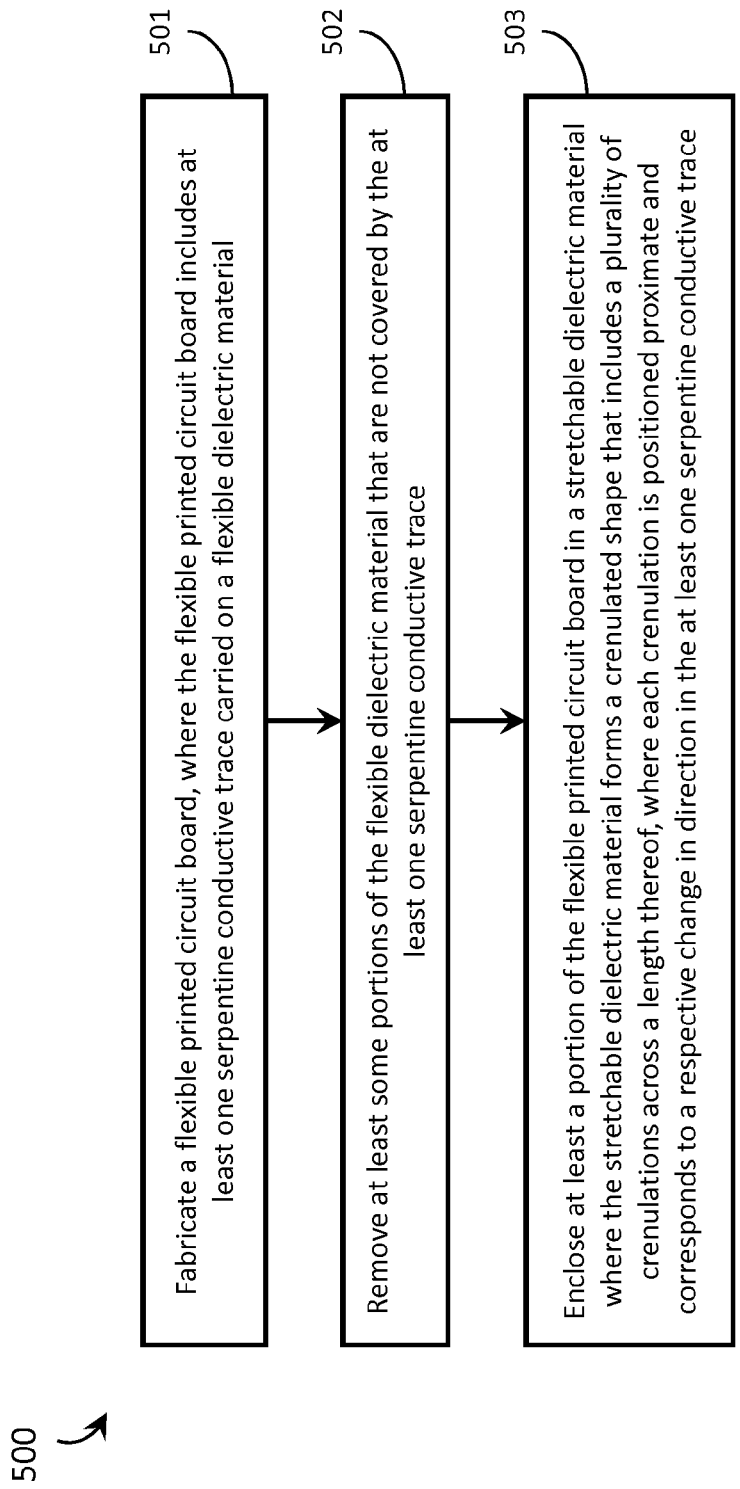
FIG. 5 is a flow-diagram showing a method of fabricating a stretchable PCB in accordance with the present systems, articles, and methods.

FIG. 5 is a flow-diagram showing a method 500 of fabricating a stretchable PCB in accordance with the present systems, articles, and methods. Method 500 includes three acts 501, 502, and 503, though those of skill in the art will appreciate that in alternative embodiments certain acts may be omitted and/or additional acts may be added. Those of skill in the art will also appreciate that the illustrated order of the acts is shown for exemplary purposes only and may change in alternative embodiments. Method 500 may be performed using conventional tools and equipment for fabricating, manufacturing, or otherwise producing PCBs.

At 501, a flexible PCB (i.e., an adapted flexible PCB as previously described) is fabricated. The flexible PCB includes at least one serpentine conductive trace carried on a flexible dielectric material, such as a polymer material like polyamide, polyimide, or polyamide-imide. As previously described, fabricating at an adapted flexible PCB may include: depositing a layer of flexible dielectric material (e.g., polyamide, polyimide, or polyamide-imide); depositing a layer of conductive metal (e.g., copper or a material including copper) on top of the flexible dielectric material; and etching a circuit pattern into the layer of conductive metal, where the circuit pattern includes at least one serpentine conductive trace.

At 502, at least some portions of the flexible dielectric material that are not covered by the at least one serpentine conductive trace are removed (e.g., cut away, die-cut, etched, etc.).

At 503, at least a portion of the flexible PCB is enclosed (e.g., enrobed, encompassed, encapsulated, laminated, or otherwise surrounded) in a stretchable dielectric material (e.g., rubber or silicone) such that the stretchable dielectric material adopts a crenulated shape that includes a plurality of crenulations across a length thereof. Each crenulation is positioned proximate and corresponds to a respective change in direction in the at least one serpentine conductive trace. The crenulated shape of the stretchable dielectric material may be "adopted" or otherwise "formed" by actively cutting-away sections of the stretchable dielectric material that are proximate respective changes in direction in the at least one serpentine conductive trace, or the crenulated shape may be produced by the act of enclosing the flexible PCB in stretchable dielectric material. For example, the flexible PCB may be placed in a mold having the desired crenulated shape and the stretchable dielectric material may be injected (in liquid form) into the mold to enclose the flexible PCB. The stretchable dielectric material may then be solidified/hardened/cured to adopt/form the crenulated shape of the mold, and the mold may be removed. A person of skill in the art will appreciate that standard practices in injection molding may necessitate a second molding stage to fill in cavities left by support structures used to hold the flexible printed circuit board in place during the first (i.e., previously described) molding stage.

The improved stretchable PCBs described herein may be used in a wide-variety of applications. A particular application described herein is in wearable electronic devices, such as wearable electromyography devices providing gesture-based control in a human-electronics interface.

Figure 6:
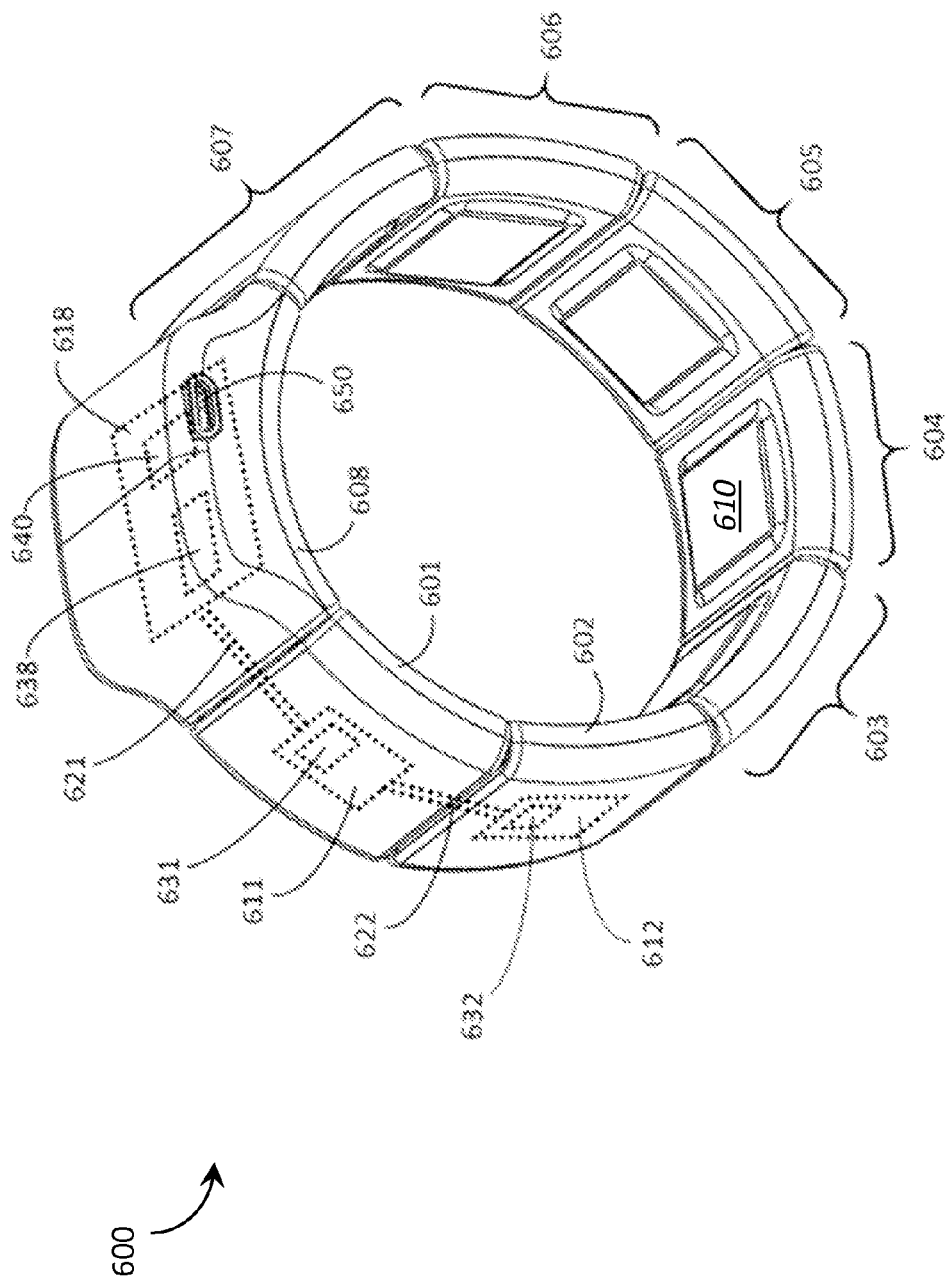
FIG. 6 is a perspective view of an exemplary wearable electronic device that employs stretchable PCBs in accordance with the present systems, articles and methods.

FIG. 6 is a perspective view of an exemplary wearable electronic device 600 that employs stretchable PCBs in accordance with the present systems, articles and methods. Exemplary device 600 is an armband designed to be worn on the wrist, forearm, or upper arm of a user, though a person of skill in the art will appreciate that the teachings described herein may readily be applied in wearable electronic devices designed to be worn elsewhere on the body of the user (such as on the leg, ankle, finger, torso, or neck of the user). Device 600 includes a set of eight pod structures 601, 602, 603, 604, 605, 606, 607, and 608 that form physically coupled links of the wearable electronic device 600. Each pod structure in the set of eight pod structures 601, 602, 603, 604, 605, 606, 607, and 608 is positioned adjacent and in between two other pod structures in the set of eight pod structures and the set of pod structures forms a perimeter of an annular or closed loop configuration. For example, pod structure 601 is positioned adjacent and in between pod structures 602 and 608 at least approximately on a perimeter of the annular or closed loop configuration of pod structures, pod structure 602 is positioned adjacent and in between pod structures 601 and 603 at least approximately on the perimeter of the annular or closed loop configuration, pod structure 603 is positioned adjacent and in between pod structures 602 and 604 at least approximately on the perimeter of the annular or closed loop configuration, and so on. Each of pod structures 601, 602, 603, 604, 605, 606, 607, and 608 is physically coupled to the two adjacent pod structures by at least one adaptive coupler (not shown in FIG. 6). For example, pod structure 601 is physically coupled to pod structure 608 by an adaptive coupler and to pod structure 602 by an adaptive coupler. The term "adaptive coupler" is used throughout this specification and the appended claims to denote a system, article or device that provides flexible, adjustable, modifiable, extendable, extensible, or otherwise "adaptive" physical coupling. Adaptive coupling is physical coupling between two objects that permits limited motion of the two objects relative to one another. An example of an adaptive coupler is an elastic material such as an elastic band. Thus, each of pod structures 601, 602, 603, 604, 605, 606, 607, and 608 in the set of eight pod structures may be adaptively physically coupled to the two adjacent pod structures by at least one elastic band. The set of eight pod structures may be physically bound in the annular or closed loop configuration by a single elastic band that couples over or through all pod structures or by multiple separate elastic bands that couple between adjacent pairs of pod structures or between groups of adjacent pairs of pod structures. Device 600 is depicted in FIG. 6 with the at least one adaptive coupler completely retracted and contained within the eight pod structures 601, 602, 603, 604, 605, 606, 607, and 608 (and therefore the at least one adaptive coupler is not visible in FIG. 6). Further details of adaptive coupling in wearable electronic devices are described in, for example, U.S. Provisional Application Ser. No. 61/860,063 (now U.S. Non-Provisional patent application Ser. No. 14/276,575), which is incorporated herein by reference in its entirety.

Throughout this specification and the appended claims, the term "pod structure" is used to refer to an individual link, segment, pod, section, structure, component, etc. of a wearable electronic device. For the purposes of the present systems, articles, and methods, an "individual link, segment, pod, section, structure, component, etc." (i.e., a "pod structure") of a wearable electronic device is characterized by its ability to be moved or displaced relative to another link, segment, pod, section, structure component, etc. of the wearable electronic device. For example, pod structures 601 and 602 of device 600 can each be moved or displaced relative to one another within the constraints imposed by the adaptive coupler providing adaptive physical coupling therebetween. The desire for pod structures 601 and 602 to be movable/displaceable relative to one another specifically arises because device 600 is a wearable electronic device that advantageously accommodates the movements of a user and/or different user forms. However, it is this movement/displacement that may put physical stress/strain on stretchable PCBs coupling between pod structures as described in more detail later.

Device 600 includes eight pod structures 601, 602, 603, 604, 605, 606, 607, and 608 that form physically coupled links of the device 600. The number of pod structures included in a wearable electronic device is dependent on at least the nature, function(s), and design of the wearable electronic device, and the present systems, articles, and methods may be applied to any wearable electronic device employing any number of pod structures, including wearable electronic devices employing more than eight pod structures, wearable electronic devices employing fewer than eight pod structures, and (unless pod structures are expressly recited in a claim) wearable electronic devices that employ configurations that do not make use of pod structures.

In exemplary device 600 of FIG. 6, each of pod structures 601, 602, 603, 604, 605, 606, 607, and 608 comprises a respective housing having a respective inner volume. Each housing may be formed of substantially rigid material and may be optically opaque. Thus, details of the components contained within the housings (i.e., within the inner volumes of the housings) of pod structures 601, 602, 603, 604, 605, 606, 607, and 608 are not visible in FIG. 6. To facilitate descriptions of exemplary device 600, some internal components are depicted by dashed lines in FIG. 6 to indicate that these components are contained in the inner volume(s) of housings and not actually visible in the view depicted in FIG. 6, unless a transparent or translucent material is used to form the housings. For example, any or all of pod structures 601, 602, 603, 604, 605, 606, 607, and/or 608 may include electric circuitry. In FIG. 6, a first pod structure 601 is shown containing electric circuitry 611 (i.e., electric circuitry 611 is contained in the inner volume of the housing of pod structure 601), a second pod structure 602 is shown containing electric circuitry 612, and a third pod structure 608 is shown containing electric circuitry 618. The electric circuitry in any or all pod structures may be communicatively coupled to the electric circuitry in at least one adjacent pod structure by at least one respective communicative pathway (e.g., by at least one electrically conductive pathway and/or by at least one optical pathway). For example, FIG. 6 shows a first communicative pathway 621 providing communicative coupling between electric circuitry 618 of pod structure 608 and electric circuitry 611 of pod structure 601, and a second communicative pathway 622 providing communicative coupling between electric circuitry 611 of pod structure 601 and electric circuitry 612 of pod structure 602. Communicative coupling between electric circuitries of adjacent pod structures in device 600 may advantageously include systems, articles, and methods for strain mitigation as described in U.S. Provisional Patent Application Ser. No. 61/857,105 (now U.S. Non-Provisional patent application Ser. No. 14/335,668), which is incorporated by reference herein in its entirety. In accordance with the present systems, articles, and methods, communicative coupling between adjacent pod structures (e.g., communicative pathways 621 and 622 from FIG. 6) may be realized through stretchable PCBs.

Throughout this specification and the appended claims, the term "rigid" as in, for example, "substantially rigid material," is used to describe a material that has an inherent tendency to maintain its shape and resist malformation/deformation under the moderate stresses and strains typically encountered by a wearable electronic device.

Each individual pod structure within a wearable electronic device may perform a particular function, or particular functions. For example, in device 600, each of pod structures 601, 602, 603, 604, 605, 606, and 607 includes a respective sensor 610 (only one called out in FIG. 6 to reduce clutter) to in use detect inputs effected by a user and to provide electrical signals in response to the detected inputs. Thus, each of pod structures 601, 602, 603, 604, 605, 606, and 607 may be referred to as a respective "sensor pod." Throughout this specification and the appended claims, the term "sensor pod" is used to denote an individual pod structure that includes at least one sensor or transducer to in use detect inputs effected by a user. Each sensor 610 may be any type of sensor that is capable of detecting any kind of signal produced, generated, or otherwise effected by the user, including but not limited to: an electromyography sensor, a magnetomyography sensor, a mechanomyography sensor, a blood pressure sensor, a heart rate sensor, a gyroscope, an accelerometer, a compass, and/or a thermometer. In exemplary device 600, each of sensor pods 601, 602, 603, 604, 605, 606, and 607 includes a respective electromyography sensor 610 (only one called out in FIG. 6 to reduce clutter) to in use detect inputs effected by the user in the form of electrical signals produced by muscle activity. Wearable electromyography device 600 may transmit information based on the detected muscle activity to provide a human-electronics interface (e.g., an HCI). Some further details of exemplary wearable electromyography device 600 are described in U.S. Provisional Patent Application Ser. No. 61/752,226 (now U.S. Non-Provisional patent application Ser. No. 14/155,107), U.S. Provisional Patent Application Ser. No. 61/768,322 (now U.S. Non-Provisional patent application Ser. No. 14/186,889), and U.S. Provisional Patent Application Ser. No. 61/771,500 (now U.S. Non-Provisional patent application Ser. No. 14/194,252), each of which is incorporated herein by reference in its entirety. Those of skill in the art will appreciate, however, that a wearable electronic device having electromyography functionality is used only as an example in the present systems, articles, and methods and that the systems, articles and methods for stretchable PCBs in wearable electronic devices described herein are in no way limited to wearable electronic devices that employ electromyography sensors unless explicitly recited in a respective claim to such.

Pod structure 608 of device 600 includes a processor 640 that in use processes the signals provided by the sensors 610 of sensor pods 601, 602, 603 604, 605, 606, and 607 in response to user-effected inputs. Pod structure 608 may therefore be referred to as a "processor pod." Throughout this specification and the appended claims, the term "processor pod" is used to denote an individual pod structure that includes at least one processor to process signals. The processor may be any type of processor, including but not limited to: a digital microprocessor or microcontroller, an application-specific integrated circuit, a field-programmable gate array, or the like, that analyzes the signals to determine at least one output, action, or function based on the signals.

As used throughout this specification and the appended claims, the terms "sensor pod" and "processor pod" are not necessarily exclusive. A single pod structure may satisfy the definitions of both a "sensor pod" and a "processor pod" and may be referred to as either type of pod structure. For greater clarity, the term "sensor pod" is used to refer to any pod structure that includes a sensor and performs at least the function(s) of a sensor pod, and the term processor pod is used to refer to any pod structure that includes a processor and performs at least the function(s) of a processor pod. In device 600, processor pod 608 includes a sensor 610 (not visible in FIG. 6) to detect inputs effected by a user, so processor pod 608 could be referred to as a sensor pod. However, in exemplary device 600, processor pod 608 is the only pod structure that includes a processor 640, thus processor pod 608 is the only pod structure in exemplary device 600 that can be referred to as a processor pod. In alternative embodiments of device 600, multiple pod structures may include processors, and thus multiple pod structures may serve as processor pods. Similarly, some pod structures may not include sensors.

As previously described, each of pod structures 601, 602, 603, 604, 605, 606, 607, and 608 may include electric circuitry. FIG. 6 depicts electric circuitry 611 inside the inner volume of sensor pod 601, electric circuitry 612 inside the inner volume of sensor pod 602, and electric circuitry 618 inside the inner volume of processor pod 608. Circuitry 611 in sensor pod 601 includes at least component 631, circuitry 612 in sensor pod 602 includes at least component 632, and circuitry 618 in processor pod 608 includes at least components 638 and 640. The components and functions of the electric circuitry in any or all of pod structures 601, 602, 603, 604, 605, 606, 607, and/or 608 depend on the nature of device 600. As previously described, component 640 of circuitry 618 in processor pod 608 may include at least one processor (e.g., at least one microprocessor, digital signal processor (DSP), graphics processing unit (GPU), application specific integrated circuit (ASIC), programmable gate array (PGA) and/or programmable logic unit (PLU)). In the example of device 600 as an electromyography device, each of pod structures 601, 602, 603, 604, 605, 606, 607, and 608 may include a respective amplification circuit to in use amplify electrical signals provided by at least one respective sensor 610. For example, each of components 631, 632, and 638 may include a respective amplification circuit to amplify electrical signals provided by at least one respective sensor 610 in each of pod structures 601, 602, and 608. In this way, sensor pod 601 (and similarly sensor pod 602 and processor pod 608) may include an electromyography sensor 610 to provide analog signals in response to muscle activity by a user, and the sensor 610 of sensor pod 601 may be communicatively coupled to an amplification circuit 631 in electric circuitry 611 to amplify the analog signals provided by the sensor 610.

The electric circuitry of any or all of pod structures 601, 602, 603, 604, 605, 606, 607, and/or 608 may include an analog-to-digital conversion ("ADC") circuit to in use convert analog signals into digital signals. Thus, any or all of components 631, 632, and 638 may further include a respective ADC circuit to convert analog signals provided by at least one respective sensor 610 in each of pod structures 601, 602, and 608 into digital signals. In this way, sensor pod 601 (and similarly sensor pod 602 and processor pod 608) may include an electromyography sensor 610 to provide analog signals in response to muscle activity by a user, the sensor 610 of sensor pod 601 may be communicatively coupled to an amplification circuit 631 in electrical circuitry 611 to amplify the analog signals provided by the sensor 610, and the amplification circuit 631 may be communicatively coupled to an ADC circuit 631 to convert the amplified analog signals into digital signals.

Processor pod 608 may be the only one of pod structures 601, 602, 603, 604, 605, 606, 607, and 608 that includes an ADC circuit 638 such that amplified analog signals are routed through communicative pathways (e.g., communicative pathways 621 and 622) to processor pod 608, or each of pod structures 601, 602, 603, 604, 605, 606, 607, and 608 may include a respective ADC circuit (e.g., 631, 632, and 638) such that digital signals are routed through communicative pathways (e.g., communicative pathways 621 and 622) to processor pod 608.

The electric circuitry (e.g., 611, 612, and/or 618) of any pod structure in device 600 may include other circuits, elements, or components, including but not limited to: filtering circuits, an optical signal generator to convert electrical signals into optical signals, an electrical signal generator to convert optical signals into electrical signals, a battery to provide a portable power source for device 600, a wireless transmitter (e.g., a Bluetooth® transmitter) to send signals to another electronic device based on the muscle activity signals detected by electromyography sensors 610, and/or a tethered connector port 650 (e.g., wired or optical) to provide a direct communicative coupling to another electronic device for the purpose of power transfer (e.g., recharging the battery) and/or data transfer. Connector port 650 is illustrated in FIG. 6 as a micro-Universal Serial Bus port, though a person of skill in the art will appreciate that any connector port may similarly be used, including but not limited to: a Universal Serial Bus port, a mini-Universal Serial Bus port, a SMA port, a THUNDERBOLT® port, and the like.

Signals that are provided by sensors 610 in device 600 are routed to processor pod 608 for processing by processor 640. In accordance with the present systems, articles, and methods, stretchable PCBs may be used to provide the communicative couplings between pod structures in device 600. Device 600 employs a plurality of communicative pathways (e.g., 621 and 622) to route the signals that are output by sensor pods 601, 602, 603, 604, 605, 606, and 607 to processor pod 608. Each respective pod structure 601, 602, 603, 604, 605, 606, 607, and 608 in device 600 is communicatively coupled to, over, or through at least one of the two other pod structures between which the respective pod structure is positioned by at least one respective communicative pathway from the plurality of communicative pathways. Each communicative pathway (e.g., 621 and 622) may include any number of communicative pathways (e.g., a single communicative pathway or multiple communicative pathways) realized by respective serpentine signal paths (i.e., respective serpentine conductive traces) in stretchable PCBs.

Figure 7:
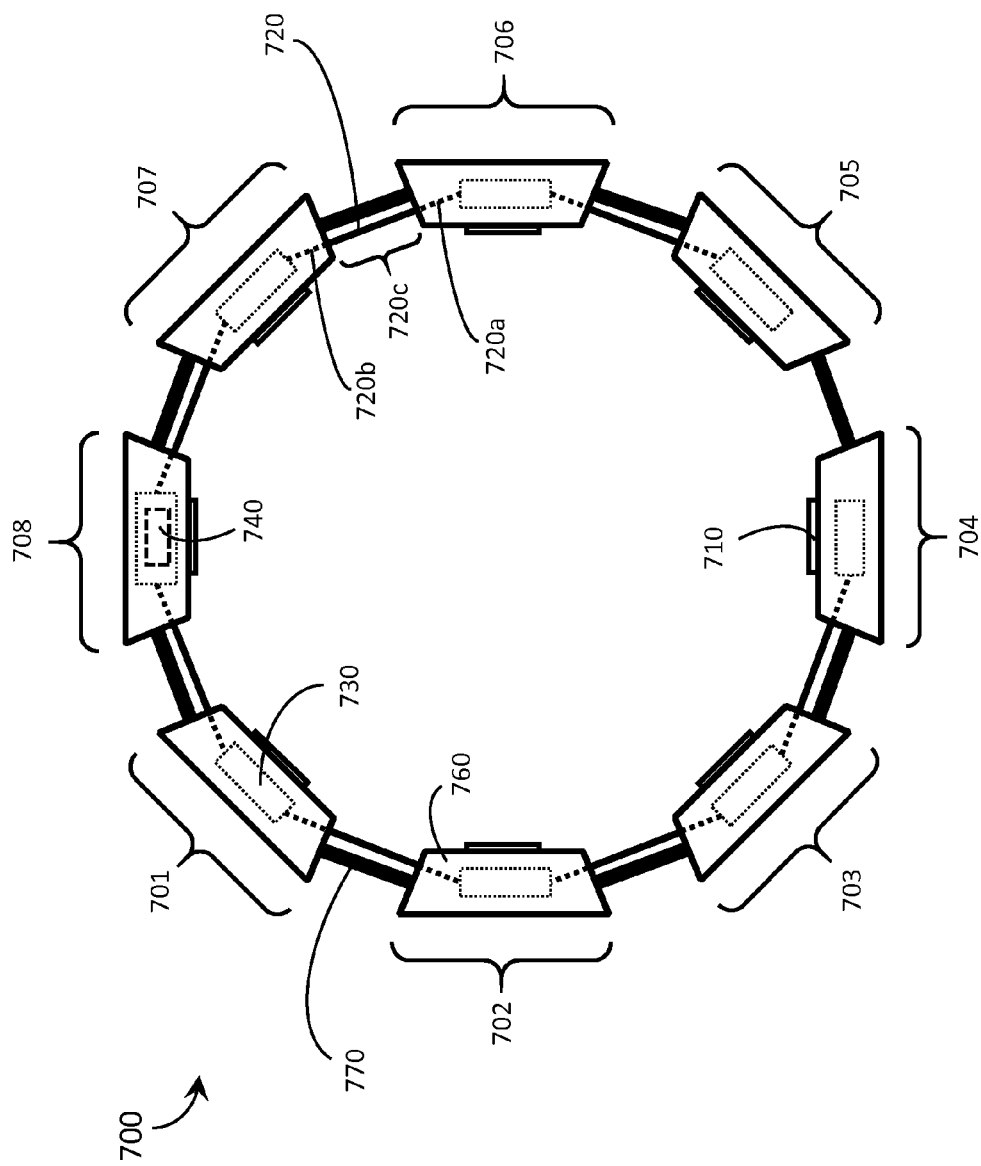
FIG. 7 is a side-elevation view of a wearable electronic device that employs stretchable PCBs in accordance with the present systems, articles, and methods.

FIG. 7 is a side-elevation view of a wearable electronic device 700 that employs stretchable PCBs in accordance with the present systems, articles, and methods. Device 700 is substantially similar to device 600 from FIG. 6 in that device 700 comprises a set of pod structures comprising sensor pods 701, 702, 703, 704, 705, 706, and 707 and processor pod 708 that form physically coupled links of wearable electronic device 700. Each pod structure is positioned adjacent and in between two other pod structures such that the set of pod structures forms a perimeter of an annular or closed loop configuration. FIG. 7 shows device 700 in an expanded annular or closed loop configuration adapted to fit the arm of a larger user than the contracted annular or closed loop configuration of device 600 from FIG. 6. As a result, adaptive couplers 770 (only one called out in FIG. 7) providing adaptive physical coupling between adjacent pairs of pod structures are visible in FIG. 7, whereas such adaptive couplers 770 are not visible in FIG. 6. Each of sensor pods 701, 702, 703, 704, 705, 706, and 707 comprises a respective sensor 710 (only one called out in FIG. 7 to reduce clutter) to in use detect inputs effected by a user (e.g., an electromyography sensor that detects muscle activity by a user) and provide signals in response to the detected inputs. Processor pod 708 comprises a similar sensor 710 as well as a processor 740 that in use processes the signals provided by the respective sensors 710. Signals provided by sensors 710 are routed from each of sensor pods 701, 702, 703, 704, 705, 706, and 707 to processor pod 708 by communicative pathways 720 (only one called out in FIG. 7 to reduce clutter). In accordance with the present systems, articles, and methods, communicative pathways 720 are implemented as one or more stretchable PCB(s) (e.g., PCB 200 from FIG. 3 or PCB 300 from FIG. 3).

Each of pod structures 701, 702, 703, 704, 705, 706, 707, and 708 comprises a respective housing 760 (only one called out in FIG. 7 to reduce clutter) formed of substantially rigid material and having an inner volume that contains at least a portion of respective electric circuitry 730 (only one called out in FIG. 7 to reduce clutter). Each of sensors 710 is positioned on or proximate a surface of a respective housing 760 and communicatively coupled to the electric circuitry 730 therein. For each of pod structures 701, 702, 703, 704, 705, 706, 707, and/or 708, electric circuitry 730 may include an amplification circuit and/or a filtering circuit and/or an ADC circuit. As previously described, housings 760 may be optically opaque, so some exemplary components within housings 760 (e.g., electric circuitry 730) are illustrated with dashed lines to indicate that such components may not actually be visible in the view illustrated in FIG. 7. Each communicative pathway 720 provides communicative coupling between the respective electric circuitries 730 in each of two pod structures 701, 702, 703, 704, 705, 706, 707, and 708. Thus, each communicative pathway 720 (i.e., each stretchable PCB 720) includes a respective first portion 720a in the inner volume of the housing 760 of a respective first pod structure (e.g., sensor pod 706), a respective second portion 720b in the inner volume of the housing 760 of a respective second pod structure (e.g., sensor pod 707), and a respective third portion 720c that extends between the housing 760 of the respective first pod structure (e.g., sensor pod 706) and the housing 760 of the respective second pod structure (e.g., sensor pod 707).

FIG. 7 shows that stretchable PCBs 720 provide routes through which signals may be coupled from each of sensor pods 701, 702, 703, 704, 705, 706, and 707 to processor pod 708. In the illustrated example of device 700, the signals output by each of sensor pods 701, 702, 703, 704, 705, 706, and 707 are serially routed to successive ones of adjacent pod structures in device 700 by stretchable PCBs 720 until the signals output by each sensor pod 701, 702, 703, 704, 705, 706, 707 are routed to processor pod 708. For example, signals output by a first sensor pod 701 are routed to processor pod 708 through a first stretchable PCB 720 that communicatively couples first sensor pod 701 to processor pod 708; signals output by a second sensor pod 702 are routed to processor pod 708 through first sensor pod 701 by a second stretchable PCB 720 that communicatively couples the second sensor pod 702 to the first sensor pod 701 and then by the first stretchable PCB 720 that communicatively couples the first sensor pod 701 to processor pod 708; and signals output by a third sensor pod 703 are routed to processor pod 708 through second sensor pod 702 and first sensor pod 701 by a third stretchable PCB 720 that communicatively couples the third sensor pod 703 to the second sensor pod 702, then by the second stretchable PCB 720 that communicatively couples the second sensor pod 702 to the first sensor pod 701, and then by the first stretchable PCB 720 that communicatively couples the first sensor pod 701 to processor pod 708; etc.

As previously described, processor 740 in processor pod 708 may advantageously process digital signals. Analog signals may first be provided by sensors 710 in response to user-effected inputs, and any or all of electric circuitries 730 may include an ADC circuit that converts the analog signals into digital signals for processing by processor 740.

In accordance with the present systems, articles, and methods, stretchable PCBs may advantageously provide communicative coupling between components in wearable electronic devices, such as wearable electromyography devices. A wearable electromyography device may employ adaptive couplers; however in accordance with the present systems, articles, and methods, stretchable PCBs may also serve as adaptive couplers. Thus, wearable electronic devices that employ stretchable PCBs may not require separate adaptive coupling devices as the function of adaptive coupling devices may be achieved by the stretchable PCBs themselves.

Furthermore, the stretchable PCBs described herein may also enable single-piece construction for all of the electrical and communicative components described for devices 600 and 700. In other words, rather than using multiple stretchable PCBs providing communicative coupling between the respective electrical circuitries of multiple pod structures, a single stretchable PCB may include all of the electric circuitry of each respective pod structure (including, e.g., EMG sensor circuitry) and provide all of the communicative pathways providing communicative coupling therebetween (and further provide the elastic/adaptive physical coupling between pod structures as described above.

Figure 8:
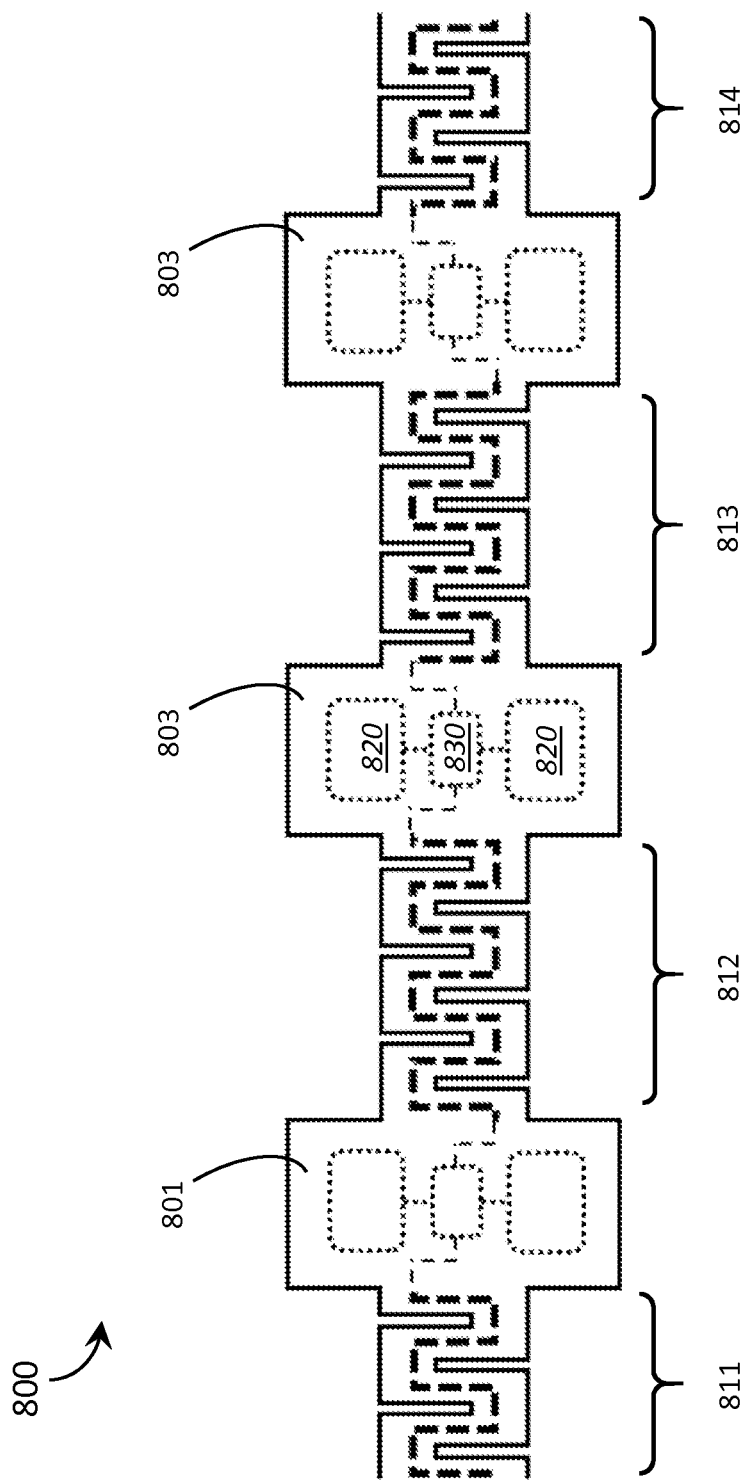
FIG. 8 is a schematic diagram of a single-piece stretchable PCB that includes wide regions respectively providing the electric circuitries of pod structures of a wearable EMG device and narrow regions respectively providing stretchable communicative coupling between adjacent pod structures in accordance with the present systems, articles, and methods.

FIG. 8 is a schematic diagram of a single-piece stretchable PCB 800 that includes wide regions 801, 802, and 803 respectively providing the electric circuitries of "pod structures" of a wearable EMG device and narrow regions 811, 812, 813, and 814 respectively providing stretchable communicative coupling between adjacent pod structures in accordance with the present systems, articles, and methods. Each of wide regions 801, 802, and 803 includes respective EMG sensors 820 (only two called out in FIG. 8 to reduce clutter) and electric circuitry 830 (only one called out in FIG. 8 to reduce clutter). Each of narrow regions 811, 812, 813, and 814 may include a respective portion of stretchable PCB that is similar to stretchable PCBs 200 and/or 300 previously described (i.e., having serpentine conductive traces enclosed in crenulated stretchable dielectric material). The single-piece construction of PCB 800 greatly simplifies the manufacturing of the corresponding wearable EMG device and provides reduced manufacturing cost (fewer manufacturing steps and fewer components), improved reliability (fewer electrical connectors and electrical connections between separate component), and improved performance.

The above description of illustrated embodiments, including what is described in the Abstract, is not intended to be exhaustive or to limit the embodiments to the precise forms disclosed. Although specific embodiments of and examples are described herein for illustrative purposes, various equivalent modifications can be made without departing from the spirit and scope of the disclosure, as will be recognized by those skilled in the relevant art. The teachings provided herein of the various embodiments can be applied to other portable and/or wearable electronic devices, not necessarily the exemplary wearable electronic devices generally described above.

For instance, the foregoing detailed description has set forth various embodiments of the devices and/or processes via the use of block diagrams, schematics, and examples. Insofar as such block diagrams, schematics, and examples contain one or more functions and/or operations, it will be understood by those skilled in the art that each function and/or operation within such block diagrams, flowcharts, or examples can be implemented, individually and/or collectively, by a wide range of hardware, software, firmware, or virtually any combination thereof. In one embodiment, the present subject matter may be implemented via Application Specific Integrated Circuits (ASICs). However, those skilled in the art will recognize that the embodiments disclosed herein, in whole or in part, can be equivalently implemented in standard integrated circuits, as one or more computer programs executed by one or more computers (e.g., as one or more programs running on one or more computer systems), as one or more programs executed by on one or more controllers (e.g., microcontrollers) as one or more programs executed by one or more processors (e.g., microprocessors), as firmware, or as virtually any combination thereof, and that designing the circuitry and/or writing the code for the software and or firmware would be well within the skill of one of ordinary skill in the art in light of the teachings of this disclosure.

When logic is implemented as software and stored in memory, logic or information can be stored on any computer-readable medium for use by or in connection with any processor-related system or method. In the context of this disclosure, a memory is a computer-readable medium that is an electronic, magnetic, optical, or other physical device or means that contains or stores a computer and/or processor program. Logic and/or the information can be embodied in any computer-readable medium for use by or in connection with an instruction execution system, apparatus, or device, such as a computer-based system, processor-containing system, or other system that can fetch the instructions from the instruction execution system, apparatus, or device and execute the instructions associated with logic and/or information.

In the context of this specification, a "non-transitory computer-readable medium" can be any element that can store the program associated with logic and/or information for use by or in connection with the instruction execution system, apparatus, and/or device. The computer-readable medium can be, for example, but is not limited to, an electronic, magnetic, optical, electromagnetic, infrared, or semiconductor system, apparatus or device. More specific examples (a non-exhaustive list) of the computer readable medium would include the following: a portable computer diskette (magnetic, compact flash card, secure digital, or the like), a random access memory (RAM), a read-only memory (ROM), an erasable programmable read-only memory (EPROM, EEPROM, or Flash memory), a portable compact disc read-only memory (CDROM), digital tape, and other non-transitory media.

The various embodiments described above can be combined to provide further embodiments. To the extent that they are not inconsistent with the specific teachings and definitions herein, all of the U.S. patents, U.S. patent application publications, U.S. patent applications, foreign patents, foreign patent applications and non-patent publications referred to in this specification and/or listed in the Application Data Sheet, including but not limited to U.S. Provisional Patent Application Ser. No. 61/872,569; U.S. Provisional Patent Application Ser. No. 61/857,105 (now U.S. Non-Provisional patent application Ser. No. 14/335,668); U.S. Provisional Patent Application Ser. No. 61/752,226 (now U.S. Non-Provisional patent application Ser. No. 14/155,107); U.S. Provisional Patent Application Ser. No. 61/768,322 (now U.S. Non-Provisional patent application Ser. No. 14/186,889); U.S. Provisional Patent Application Ser. No. 61/771,500 (now U.S. Non-Provisional patent application Ser. No. 14/194,252); U.S. Provisional Application Ser. No. 61/860,063 (now U.S. Non-Provisional patent application Ser. No. 14/276,575); U.S. Provisional Application Ser. No. 61/866,960 (now U.S. Non-Provisional patent application Ser. No. 14/461,044); and U.S. Provisional Patent Application Ser. No. 61/869,526 (now U.S. Non-Provisional patent application Ser. No. 14/465,194), are incorporated herein by reference, in their entirety. Aspects of the embodiments can be modified, if necessary, to employ systems, circuits and concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method of fabricating a stretchable printed circuit board, the method comprising:
fabricating a flexible printed circuit board, wherein fabricating a flexible printed circuit board comprises:
depositing a layer of flexible dielectric material;
depositing a layer of conductive metal on top of the flexible dielectric material; and
etching a circuit pattern into the layer of conductive metal, wherein the circuit pattern includes at least one serpentine conductive trace that includes a plurality of changes in direction,
removing at least some portions of the flexible dielectric material that are not covered by the at least one serpentine conductive trace; and
enclosing at least a portion of the flexible printed circuit board in a stretchable dielectric material, wherein the stretchable dielectric material forms a crenulated shape that includes a plurality of crenulations across a length thereof, wherein each crenulation is positioned proximate and corresponds to a respective change in direction in the at least one serpentine conductive trace, and wherein enclosing at least a portion of the flexible printed circuit board in a stretchable dielectric material comprises:
placing the flexible printed circuit board into a mold that provides a crenulated shape for the stretchable dielectric material;
injecting the stretchable dielectric material, in liquid form, into the mold;
solidifying the stretchable dielectric material; and
removing the mold.

2. The method of claim 1 wherein removing at least some portions of the flexible dielectric material that are not covered by the at least one serpentine conductive trace includes cutting away the at least some portions of the flexible dielectric material that are not covered by the at least one serpentine conductive trace.

* * * * *